US 7,670,281 B2

(12) United States Patent
Kronner

(10) Patent No.: US 7,670,281 B2
(45) Date of Patent: Mar. 2, 2010

(54) INSTRUMENT SUPPORT APPARATUS

(76) Inventor: Richard F. Kronner, 1443 Upper Cleveland Rapids Rd., Roseburg, OR (US) 97470

( * ) Notice: Subject to any disclaimer, the term of this patent is extended or adjusted under 35 U.S.C. 154(b) by 1181 days.

(21) Appl. No.: 11/245,509

(22) Filed: Oct. 7, 2005

(65) Prior Publication Data
US 2006/0079864 A1 Apr. 13, 2006

Related U.S. Application Data

(60) Provisional application No. 60/616,920, filed on Oct. 7, 2004.

(51) Int. Cl.
A61B 1/00 (2006.01)
E04G 3/00 (2006.01)
A61B 19/00 (2006.01)
(52) U.S. Cl. .................. 600/102; 248/278.1; 248/279.1; 606/130
(58) Field of Classification Search ................. 600/102, 600/219; 248/278.1, 279.1; 606/130
See application file for complete search history.

(56) References Cited

U.S. PATENT DOCUMENTS

| 114,243 | A | 4/1871 | Wood et al. |
| 373,362 | A | 11/1887 | Hamilton |
| 1,084,427 | A | 1/1914 | Hanks |
| 1,403,863 | A | 1/1922 | Peat |
| 4,142,632 | A | 3/1979 | Sandel |
| 4,170,336 | A | 10/1979 | Malis |
| D263,076 | S | 2/1982 | Sandel |
| D263,745 | S | 4/1982 | Sandel |
| 4,355,631 | A | 10/1982 | LeVahn |
| 4,417,710 | A | 11/1983 | Adair |
| D275,229 | S | 8/1984 | Sanderson et al. |
| 4,573,452 | A | 3/1986 | Greenberg |
| 4,596,329 | A | 6/1986 | Eldridge, Jr. |
| 4,597,493 | A | 7/1986 | Bruso |
| 4,617,916 | A | 10/1986 | LeVahn et al. |
| 4,863,133 | A | 9/1989 | Bonnell |
| 4,867,404 | A | 9/1989 | Harrington et al. |
| D306,481 | S | 3/1990 | Lang |
| 5,082,111 | A | 1/1992 | Corbitt, Jr. et al. |
| 5,104,103 | A | 4/1992 | Auchinleck et al. |
| 5,186,174 | A | 2/1993 | Schlöndorff et al. |
| 5,205,522 | A | 4/1993 | Nakamura |
| 5,224,680 | A | 7/1993 | Greenstein et al. |
| 5,284,130 | A | 2/1994 | Ratliff |
| 5,380,338 | A | 1/1995 | Christian |

(Continued)

OTHER PUBLICATIONS

Letter received Jan. 17, 2006 from Richard F. Kronner, M.D.

(Continued)

Primary Examiner—Linda C Dvorak
Assistant Examiner—Alireza Nia
(74) Attorney, Agent, or Firm—Kolisch Hartwell, P.C.

(57) ABSTRACT

An instrument support apparatus is disclosed. In some embodiments, the instrument support apparatus may be for supporting an instrument having a shaft extending along a shaft axis relative to a patient positioned adjacent to an external frame. In some embodiments, the instrument support apparatus may include a base fixedly mountable onto the external frame, a pivot assembly mounted for pivoting relative to the base, an arm assembly extending along a longitudinal axis, and a support assembly configured to support the instrument on the arm assembly.

34 Claims, 18 Drawing Sheets

U.S. PATENT DOCUMENTS

| | | | |
|---|---|---|---|
| 5,383,637 | A | 1/1995 | Biber |
| D358,642 | S | 5/1995 | Michelson |
| 5,441,042 | A | 8/1995 | Putman |
| 5,494,034 | A | 2/1996 | Schlöndorff et al. |
| 5,513,827 | A | 5/1996 | Michelson |
| 5,558,622 | A | 9/1996 | Greenberg |
| 5,571,072 | A * | 11/1996 | Kronner .................. 600/102 |
| 5,649,946 | A | 7/1997 | Bramlet |
| 5,662,300 | A | 9/1997 | Michelson |
| 5,681,325 | A | 10/1997 | Hasson |
| 5,785,643 | A | 7/1998 | Lynn |
| 5,810,712 | A | 9/1998 | Dunn |
| 5,810,864 | A | 9/1998 | Schaller |
| 5,824,007 | A | 10/1998 | Faraz et al. |
| 5,836,453 | A | 11/1998 | Herrera |
| 5,876,325 | A | 3/1999 | Mizuno et al. |
| 5,918,844 | A | 7/1999 | Ognier |
| 5,957,423 | A * | 9/1999 | Kronner .................. 248/278.1 |
| 6,080,181 | A | 6/2000 | Jensen et al. |
| 6,200,263 | B1 | 3/2001 | Person |
| 6,213,671 | B1 | 4/2001 | Chang |
| 6,413,264 | B1 | 7/2002 | Jensen et al. |
| 6,461,372 | B1 | 10/2002 | Jensen et al. |
| 6,540,739 | B2 | 4/2003 | Lechot |
| 6,575,298 | B1 | 6/2003 | McArthur et al. |
| 6,610,009 | B2 | 8/2003 | Person |
| 6,613,039 | B1 | 9/2003 | Namba |
| 6,632,170 | B1 * | 10/2003 | Bohanan et al. ............. 600/102 |
| 6,716,163 | B2 | 4/2004 | Muhanna et al. |
| 6,966,876 | B2 | 11/2005 | Irion et al. |
| 6,969,192 | B1 | 11/2005 | Hollowell |
| 7,179,225 | B2 * | 2/2007 | Shluzas et al. ............. 600/219 |

OTHER PUBLICATIONS

Armstrong Healthcare Limited ad for EndoAssist.
Thompson Surgical Instruments, Inc., Thompson Scope Holder.
Thompson Surgical Instruments, Inc., Flexbar/Thompson Scope Holder.
Mediflex ad for surgical devices.
*Smooth Operator: The Surgical Robot*, UCI Medical Center.
*Camera and Instrument Holders and Their Clinical Value in Minimally Invasive Surgery*, Surgical Laparoscopy Endoscopy & Percutaneous Techniques, Lippincott Williams & Wilkins, 2004.
*A Passive Positioning and Supporting Device for Surgical Robots and Instrumentation*, A. Grey Lerner et al.
Summary for SightFix, World of Medicine Lemke GmbH, Mar. 18, 2003.

* cited by examiner

INSTRUMENT SUPPORT APPARATUS

CROSS-REFERENCE TO RELATED APPLICATIONS

This application claims priority under 35 U.S.C. §119(e) to U.S. Provisional Patent Application Ser. No. 60/616,920 entitled "Two Axis Pivot with Pneumatic Lock and Grip," filed Oct. 7, 2004, the complete disclosure of which is herein incorporated by reference for all purposes.

BACKGROUND OF THE DISCLOSURE

Laparoscopic surgery is a procedure in which surgical instruments and a viewing scope, referred to generally as an endoscope and more specifically as a laparascope, are inserted through small puncture wounds or incisions into the abdominal cavity of a patient. A small video camera is attached to the laparascope and connected to a television monitor for viewing the procedure.

The instruments and the laparoscope may be inserted through cannulae, which are first inserted through the incisions. Cannulae are hollow tubes with gas valves. The cannulae are left in the puncture wounds throughout the procedure. The cannulae allow the instruments and the scope to be removed and reinserted as necessary. To aid in visualizing the intraabdominal structures, gas is inserted through one of the cannulae to raise the abdominal wall. Seals are required at the exit points of the scope and instruments to prevent the gas from escaping.

The viewing laparoscope may be inserted through a cannula, which is usually inserted through an incision made in the umbilicus. The scope is then directed towards the pelvis for pelvic surgery or towards the liver for gallbladder surgery. Throughout the procedure the surgeon, assistant surgeon, or a scrub nurse must hold the scope and direct it at the target of the surgery, which typically entails constantly repositioning the scope to obtain the best view. This process ties up one hand of the surgeon or assistant surgeon, if either holds the scope. The scrub nurses also have other tasks to perform so holding the scope interferes with performing these tasks. Additionally, the surgeon typically finds it difficult to direct others to position the scope for the best view. As a result, the scope is often misdirected when not held by the surgeon.

SUMMARY OF THE INVENTION

Some embodiments may provide an instrument support apparatus for supporting an instrument having a shaft extending along a shaft axis relative to a patient positioned adjacent to an external frame. In some embodiments, the instrument support apparatus may include a base fixedly mountable onto the external frame, a pivot assembly mounted relative to the base and including a frame and a first pivot element mounted for pivoting relative to the frame about a first pivot axis, an arm assembly extending along a longitudinal axis and having a first portion mounted to the first pivot element for pivoting relative to the frame, and a second portion spaced from the first portion, a support assembly mounted to the second portion and configured to support the instrument on the arm assembly, and a first lock assembly mounted to the frame and configured to be remotely actuated to lock the first pivot element. The first lock assembly may include first and second opposing planar faces, a first stop, and a biasing mechanism. The first face may be mounted to the first pivot element for co-pivoting with the first pivot element and the second face may be disposed to move normal to the first face. The first stop may be configured to prevent pivoting of the second face about the first pivot axis and the biasing mechanism may be configured to selectively bias the second face towards the first face.

In some embodiments, the instrument support apparatus may include a base fixedly mountable onto the external frame, a pivot assembly mounted relative to the base and having a pivot element, where the pivot element is configured to pivot relative to the base about a pivot axis, an arm assembly extending along a longitudinal axis, a support assembly configured to support the instrument on the arm assembly; and an arm grip configured to releasably secure the arm assembly to the pivot element. The arm grip may include a first mounting element configured to move between a first position in which the pivot element is secured relative to the arm grip while allowing movement of the arm assembly relative to the arm grip, and a second position in which both the pivot element and the arm assembly are secured relative to the arm grip.

In some embodiments, the instrument support apparatus may include a base fixedly mountable onto the external frame, a pivot assembly mounted for pivoting relative to the base, an arm assembly extending along a longitudinal axis and having a first portion mounted for pivoting relative to the pivot assembly and a second portion spaced from the first portion, and a grip mounted to the second portion of the arm assembly and configured to support the instrument with the shaft axis extending along a support axis. The grip may include a recess extending along the support axis, the recess having an opening extending laterally of the support axis and sized to laterally receive the shaft of the instrument.

DETAILED DESCRIPTION OF THE DISCLOSURE

Figure 1:
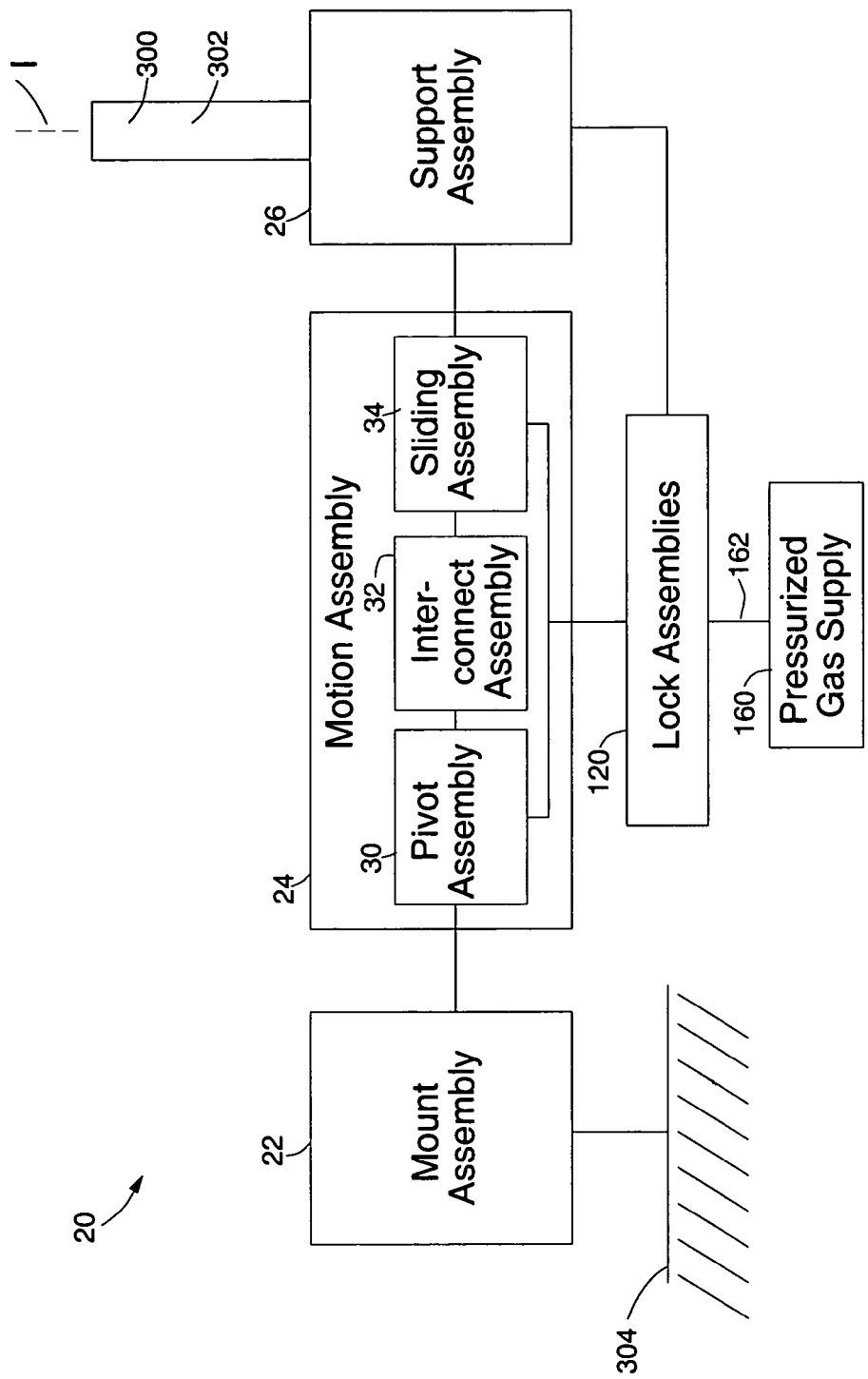
FIG. 1 is a schematic view of an instrument support apparatus.
Figure 2:
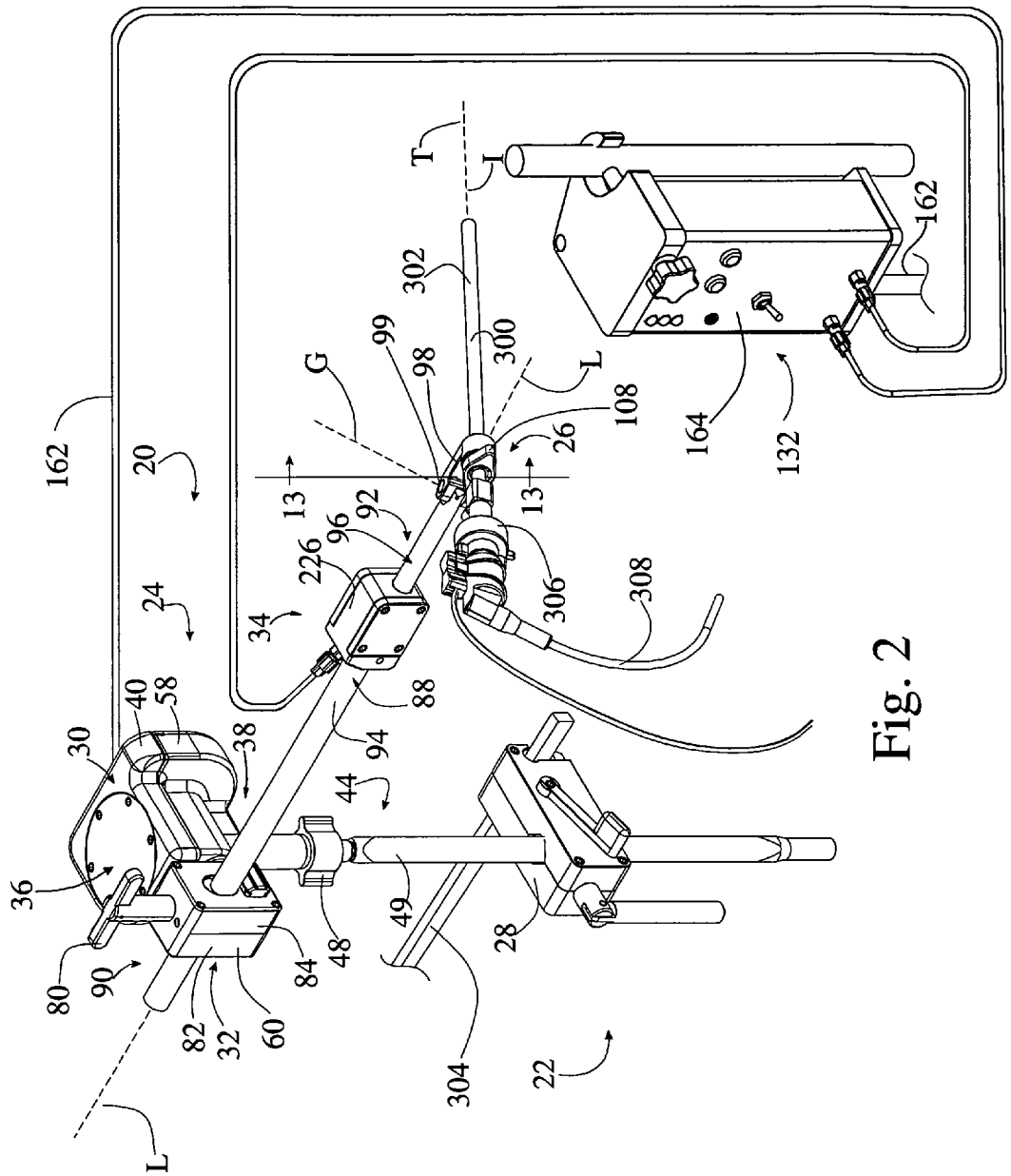
FIG. 2 is an isometric view of an illustrative example of the instrument support apparatus of FIG. 1

FIGS. 1-2 depict some embodiments of an instrument support apparatus 20. The instrument support apparatus may support an instrument 300, such as endoscope 302, relative to an operating table having an external frame 304 (such as a rail). The instrument extends along an instrument shaft axis I. The endoscope may include a camera 306 with its attached light line 308, which may be connected to remote monitoring equipment. The endoscope may be inserted into a cannula (not shown), which includes any suitable structure configured to allow instruments to be removed and reinserted into the patient as necessary. Although instrument support apparatus 20 is shown to be supporting a particular instrument, namely an endoscope, the instrument support apparatus may additionally, or alternatively, be configured to support one or more other instruments, including equipment of any appropriate form, as well.

The instrument support apparatus may include a mount assembly 22, a motion assembly 24, and a support assembly 26, as shown in FIG. 1. Mount assembly 22 may include any suitable structure configured to secure the instrument support apparatus to external frame 304. For example, the mount assembly may include a base 28, as shown in FIG. 2. The base may be fixedly mountable onto external frame 304 or may be secured to the external frame in any other suitable way. A patient may be positioned adjacent to the external frame.

Base 28 includes suitable structure known in the art. Illustrative examples of suitable structures are disclosed in U.S. Pat. No. 5,957,423, the complete disclosure of which is hereby incorporated by reference for all purposes. Although mount assembly 22 is shown to be mounted on a particular external frame, the mount assembly may be configured to be mounted on any suitable type of rigid structure.

Motion assembly 24 may include any suitable structure configured to allow a user to move instrument 300 in any predetermined way(s). For example, motion assembly 24 may include a pivot assembly 30, an interconnect assembly 32, and a sliding assembly 34, as shown in FIG. 1. Although motion assembly 24 is shown to include particular assemblies configured to allow instrument 300 to be pivoted and/or slid, the motion assembly may include any suitable assembly or combination of assemblies for any suitable movement(s). For example, motion assembly 24 may include only a pivot assembly or only a sliding assembly. Additionally, or alternatively, the motion assembly may include two or more pivot assemblies and/or two or more sliding assemblies.

Figure 3:
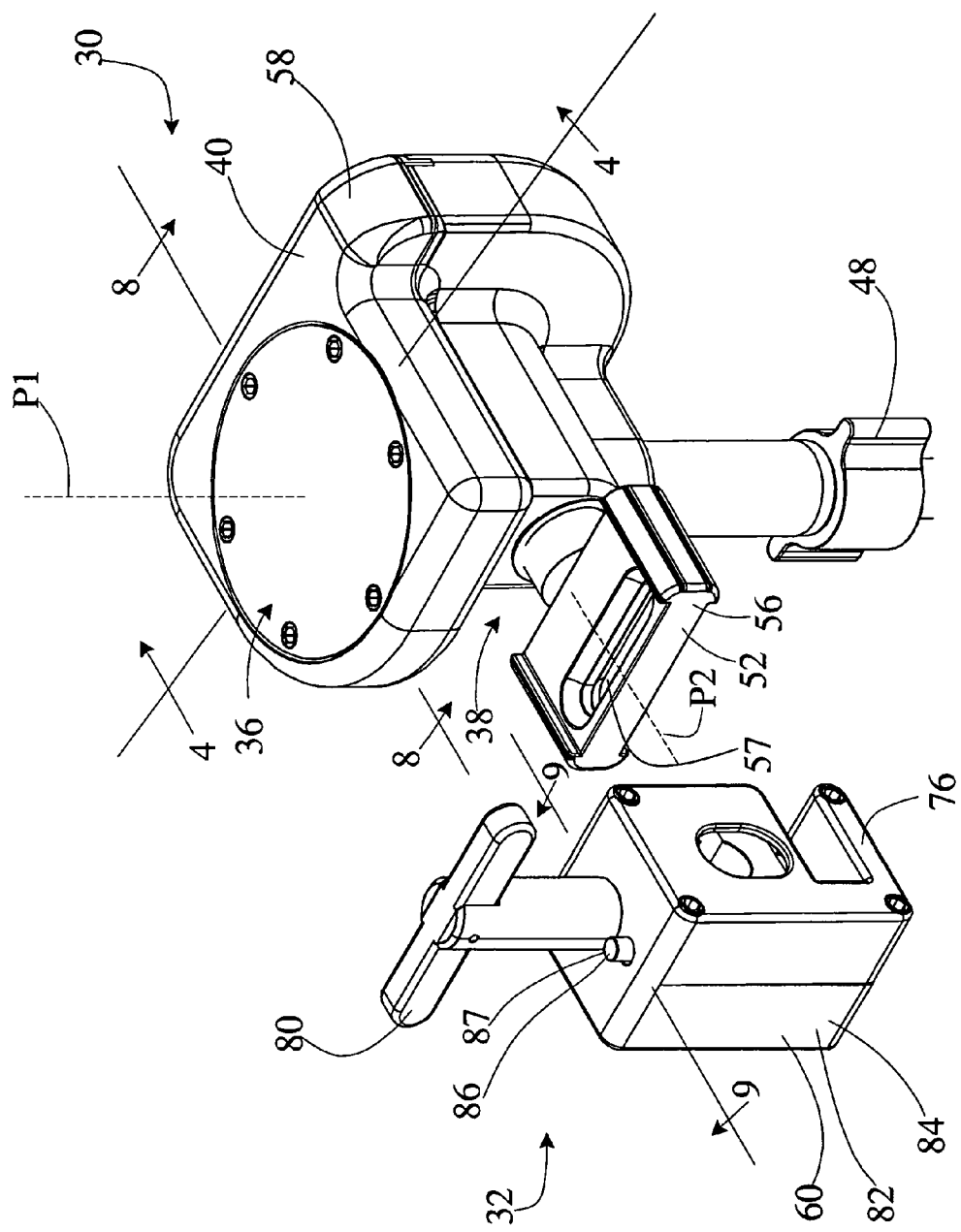
FIG. 3 is a partial isometric view of the instrument support apparatus of FIG. 2 showing a pivot assembly and an arm grip.
Figure 4:
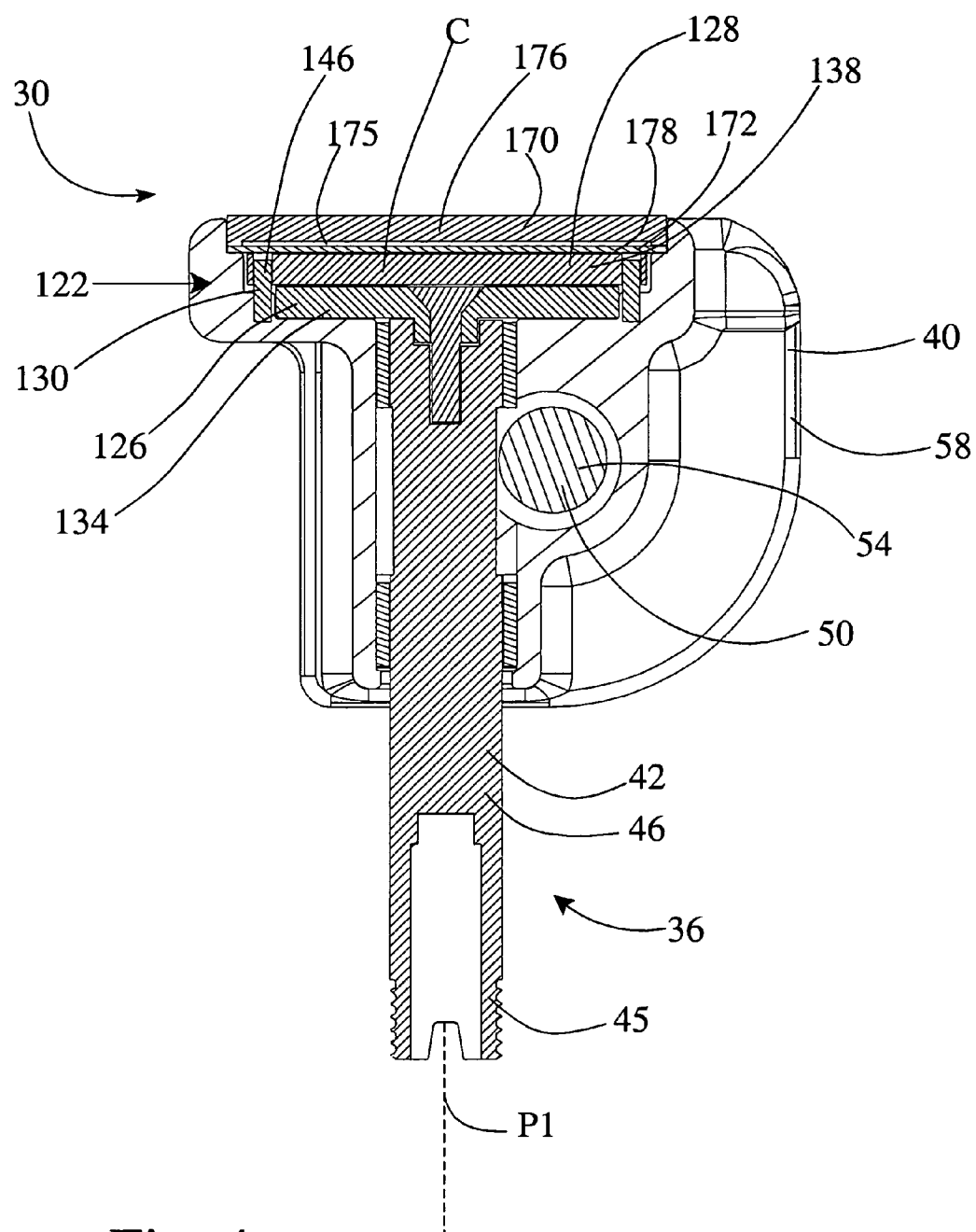
FIG. 4 is a cross-sectional view of the pivot assembly of the instrument support apparatus of FIG. 2 taken along lines 4-4 shown in FIG. 3, showing a lock assembly in the locking position.

Pivot assembly 30 may include any suitable structure configured to allow a user to pivot instrument 300 relative to mount assembly 22 about any suitable axis or axes. For example, the pivot assembly may include a first pivot structure 36, a second pivot structure 38, and a frame 40, as shown in FIGS. 4-7. First pivot structure 36 may include any suitable structure configured to allow a user to pivot instrument 300 about a first pivot axis P1, as shown in FIG. 3. For example, first pivot structure 36 may include a first pivot element 42 and a first connector 44, as shown in FIGS. 2 and 4.

First pivot element 42 may include any suitable structure configured to allow a user to pivot instrument 300 about a first pivot axis P1. For example, first pivot element 42 may include a first pivot shaft 46. First connector 44 may include any suitable structure configured to connect an end portion 45 of the first pivot element to mount assembly 22. For example, the first connector may include a connection joint 48 and an upright 49.

Figure 7:
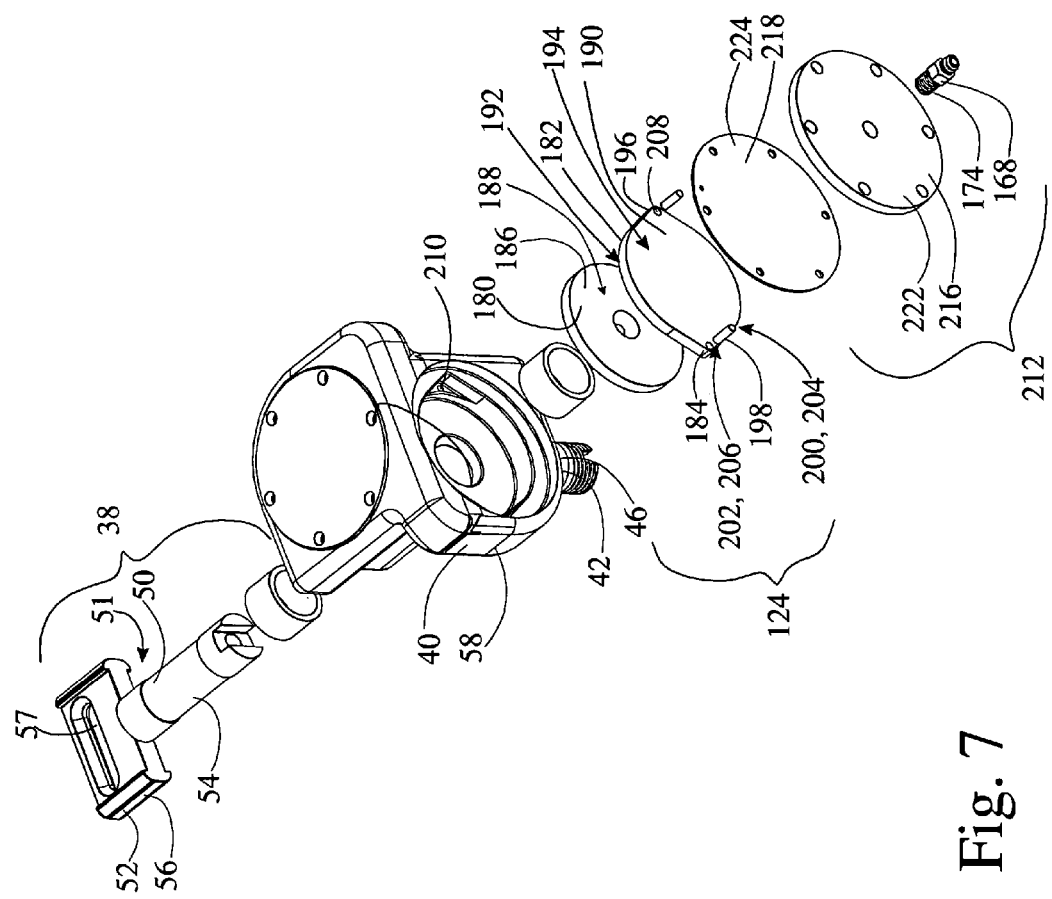
FIG. 7 is an exploded view of a second pivot structure and a second lock assembly of the pivot assembly of the instrument support apparatus of FIG. 2.

Second pivot structure 38 may include any suitable structure configured to allow a user to pivot instrument about a second pivot axis P2, as shown in FIG. 3. For example, second pivot structure 38 may include a second pivot element 50 and a second connector 52, as shown in FIG. 7. Second pivot element 50 may include any suitable structure configured to allow a user to pivot instrument 300 about a second pivot axis P2. For example, second pivot element 50 may include a second pivot shaft 54.

Second connector 52 may include any suitable structure configured to connect an end portion 51 of the second pivot element to interconnect assembly 32. For example, the second connector may include an arm grip receiver 56, as shown in FIGS. 3 and 7. The arm grip receiver may include an opening or recess 57 to facilitate the connection with the interconnect assembly. For example, the recess may receive an extension of the interconnect assembly (as described below) to secure or hold the pivot assembly to the interconnect assembly. Although arm grip receiver 56 is shown to include recess 57, the arm grip receiver may include any suitable structure configured to connect the pivot assembly to the interconnect assembly. For example, arm grip receiver may additionally, or alternatively, include an extension or any other suitable structure(s) configured to engage the interconnect assembly.

The first and second pivot axes may be along any suitable axes. For example, second pivot axis P2 may be perpendicular or transverse to first pivot axis P1 (when viewed in a plane parallel to one of the axes). For example, the first pivot axis may be along a vertical axis and the second pivot axis may be along a horizontal axis (in which case the axes are referred to as being perpendicular even if they do not intersect). Although the first and second pivot axes are shown to be perpendicular to each other, the first and second pivot axes may have any suitable relationship to each other, and may or may not intersect. For example, the second pivot axis may be at a 45-degree angle relative to the first pivot axis. Additionally, although the first and second pivot axes are shown to be vertical and horizontal, respectively, the first and second pivot axes may have any suitable orientation.

Pivot assembly 30 also may include frame 40, which may include any suitable structure configured to support and/or at least partially contain first pivot structure 36, second pivot structure 38, and/or any other components of pivot assembly 30. For example, the frame may include a housing 58, which may at least substantially enclose the first and second pivot elements, while exposing the first and second connectors. The frame also may at least substantially enclose one or more locking assemblies, as further discussed below. Although the frame is shown to include housing 58, frame 40 may include any suitable structure configured to support and/or at least partially contain one or more other components of the pivot assembly.

Although the first and second pivot structures are shown to include specific structure, any suitable structure configured to allow a user to pivot instrument 300 about any suitable pivot axis or axes may be used. Additionally, although pivot assembly 30 is shown to include two pivot structures, the pivot assembly may include more or fewer pivot structures.

Interconnect assembly 32 may include any suitable structure configured to operatively connect pivot assembly 30 and sliding assembly 34. For example, interconnect assembly may include an arm grip 60, as shown in FIGS. 3 and 9-12. In this particular example, the arm grip may include any suitable structure configured to releasably secure sliding assembly 34 to pivot assembly 30. For example, arm grip 60 may include a first mounting element 62, a second mounting element 64, a base element 66, and one or more bias elements 68. The first and second mounting elements may be slidable in a channel 69 in base element 66.

First mounting element 62 may include any suitable structure configured to secure the sliding assembly to the arm grip. For example, first mounting element 62 may include an upper arm 70. Additionally, first mounting element 62 may be movable among a plurality of positions, including an unsecured position U1 (as shown in FIG. 9) in which the first and second mounting elements freely receive arm assembly portion 90 (as described below), allowing movement of the sliding assembly relative to the arm grip, and a secured position S1 (as shown in FIG. 11) in which the first mounting element engages the sliding assembly to secure that assembly relative to the arm grip.

Second mounting element 64 may provide multiple functions, and for example, may include any suitable structure configured to assist in securing the pivot assembly to the base element and/or supporting the sliding assembly. For example, the second mounting element may include a lower arm or receiver grip 72. The lower arm may include a cavity 73 and an extension 74. The cavity may be configured to receive and conform to an arm portion of the sliding assembly. For example, one or more components of the sliding assembly may be supported in the cavity and/or may be positioned between the first and second mounting elements. Extension 74 may be configured to engage recess 57 of arm grip receiver 56 to hold or secure the arm grip receiver between the second mounting element and the base element. Although the second mounting element is shown to include extension 74, the second mounting element may additionally, or alternatively, include a recess or any other suitable structure(s) configured to engage arm grip receiver 56 and/or any suitable portion(s) of pivot assembly 30.

Figure 9:
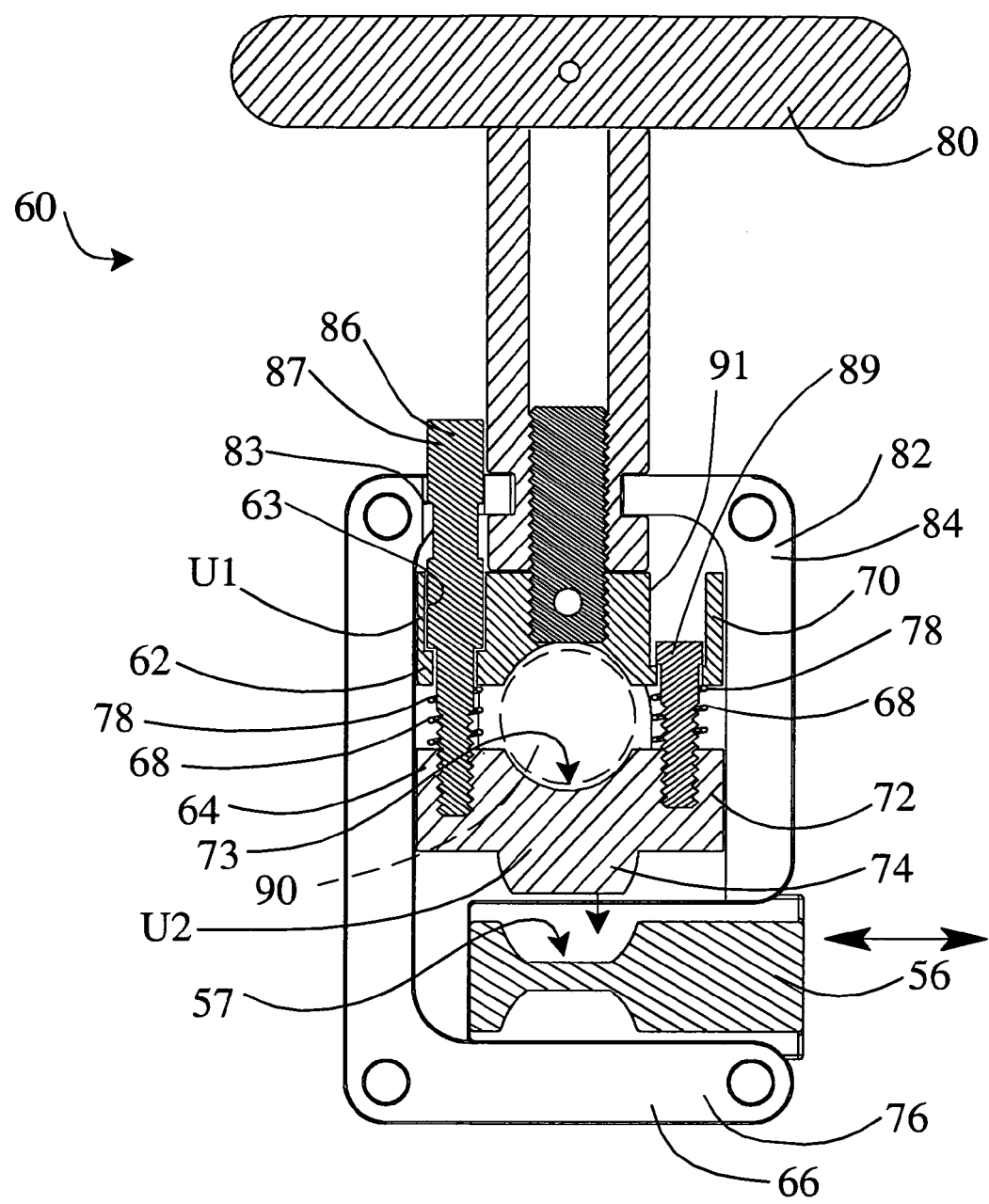
FIG. 9 is a cross-sectional view of the arm grip of the instrument support apparatus of FIG. 2 taken along lines 9-9 shown in FIG. 3, showing a first mounting element in an unsecured position and a second mounting element in an unsecured position.
Figure 10:
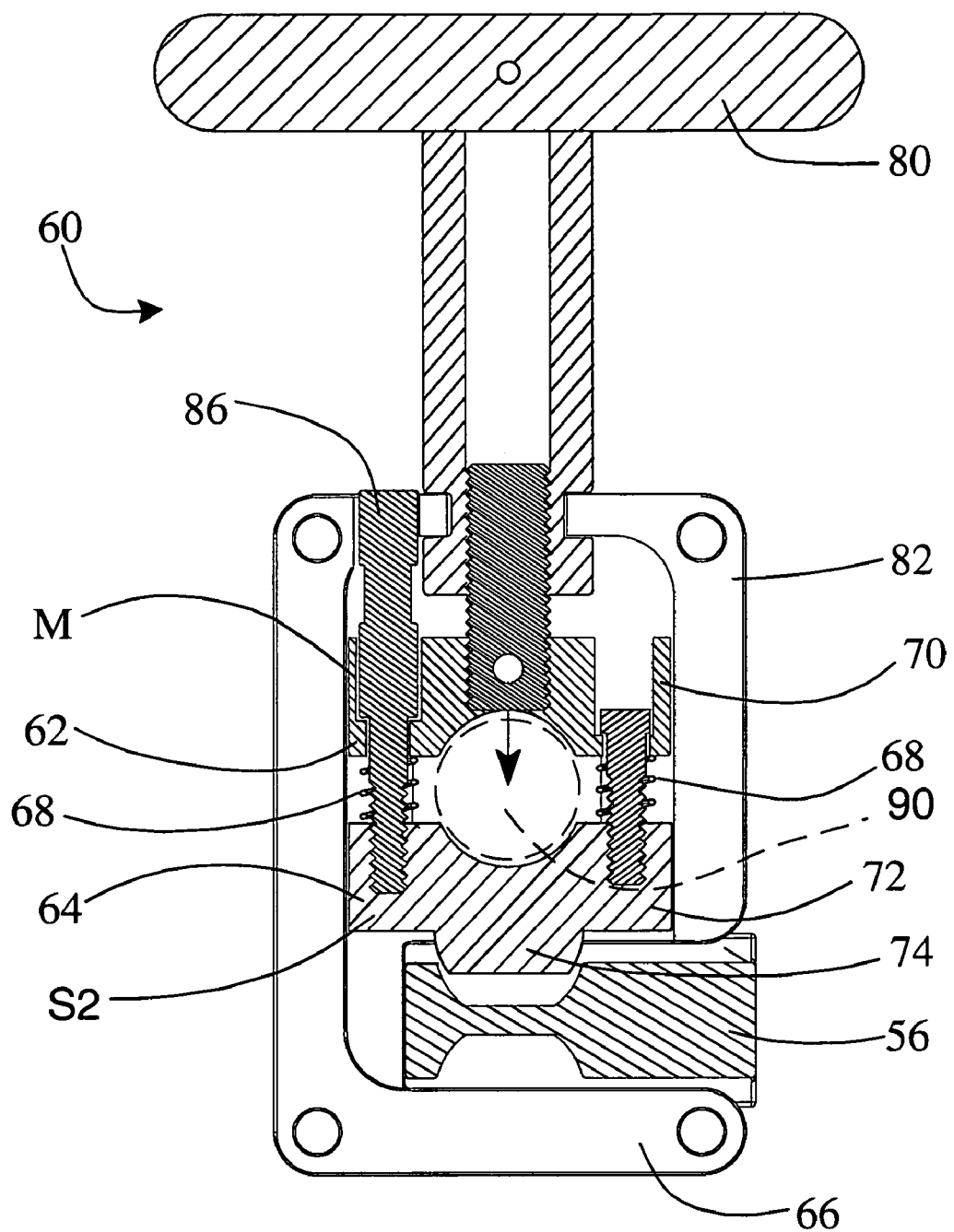
FIG. 10 is a cross-sectional view of the arm grip of the instrument support apparatus of FIG. 2 taken along lines 9-9 shown in FIG. 3, showing the arm grip attached to an arm grip receiver of a pivot assembly, the first mounting element in an intermediate position, and the second mounting element in a secured position.
Figure 11:
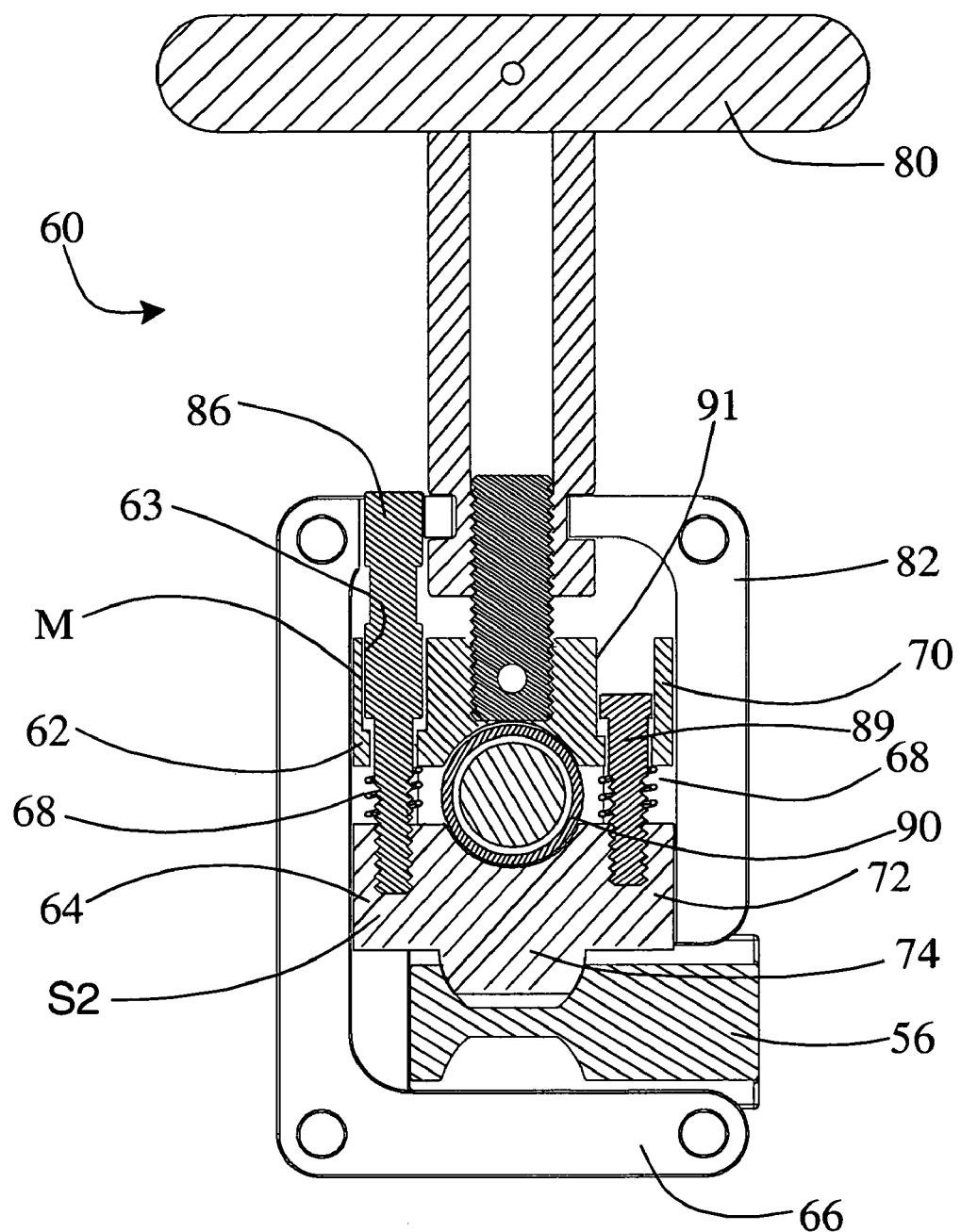
FIG. 11 is a cross-sectional view of the arm grip of the instrument support apparatus of FIG. 2 taken along lines 9-9 shown in FIG. 3, showing the arm grip attached to an arm grip receiver of a pivot assembly and to an arm assembly, the first mounting element in a secured position, and the second mounting element in a secured position.
Figure 12:
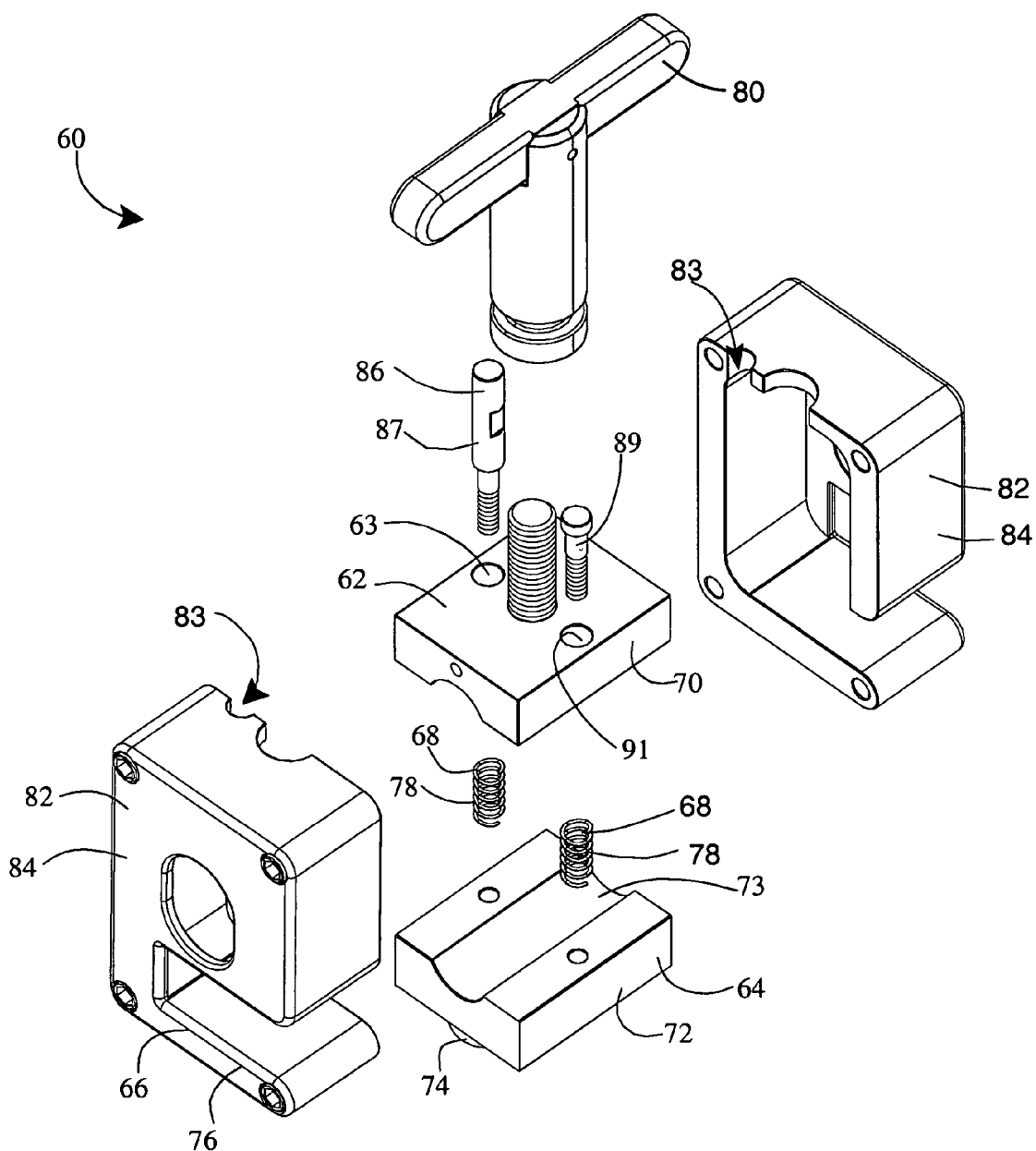
FIG. 12 is an exploded view of the arm grip of the instrument support apparatus of FIG. 2.

Additionally, second mounting element 62 may be movable among a plurality of positions, including an unsecured position U2 (as shown in FIG. 9) in which the second mounting element may be spaced from the pivot assembly allowing movement of the pivot assembly relative to the arm grip, and a secured position S2 (as shown in FIGS. 10 and 11) in which the second mounting element may engage the pivot assembly to secure that assembly relative to the arm grip.

Base element 66 may include any suitable structure configured to mount the interconnect assembly to the pivot assembly. For example, base element 66 may include a platform 76, which may attach to arm grip receiver 56 of pivot assembly 30. The arm grip receiver may thus be held between second mounting element 64 and base element 66. Those elements also may be configured such that arm grip 60 may be attached to arm grip receiver 56 even with a bag or drape (such as a sanitary bag, not shown) covering the pivot assembly.

The arm grip also may include one or more bias elements 68, which may include any suitable structure configured to operatively connect the first and second mounting elements, such as to urge the first and second mounting elements apart. For example, bias elements 68 may include one or more coiled springs 78. Although bias elements 68 are shown to include coiled springs, the bias elements may include any suitable structure configured to urge the first and second mounting elements apart, such as leaf springs, musical wire, and/or any other suitable resilient or mechanical structure.

The arm grip may include any suitable structure configured to maintain bias elements 68 in position between the first and second mounting elements. For example, a first stud 87 located in a channel 63 of the first mounting element and a second stud 89 located in a channel 91 of the first mounting element may maintain those bias elements in position between the first and second mounting elements. Although the arm grip is shown to include the first and second studs, the arm grip may include any suitable structure configured to maintain bias elements 68 in position between the first and second mounting elements.

The bias elements may be configured to allow a user to adjust the first and second mounting elements by moving the first mounting element. For example, the first mounting element may be configured to move among unsecured position U1, secured position S1, and an intermediate position M (shown in FIG. 10). As discussed above, in the unsecured position, the first mounting element may be sufficiently spaced from an arm portion of the sliding assembly to allow free receipt of the arm portion between the first and second mounting elements. The bias elements may urge the first and second mounting elements apart. In the secured position, the first mounting element may secure the sliding assembly to the arm grip by pressing the arm portion of the sliding assembly against the second mounting element, overcoming the urging of the bias elements. In turn, the second mounting element may press arm grip receiver 56 against platform 76, with extension 74 in recess 57, and thereby securing the pivot assembly and the arm grip.

In the intermediate position, the first mounting element may be spaced sufficiently from the second mounting element to freely receive the arm portion of the sliding assembly. The bias elements urge the first and second mounting elements apart. The second mounting element may thereby be urged toward the secured position S2 securing arm grip receiver 56 by insertion of extension 74 in recess 57 of the receiver.

Although first mounting element 62 is shown to be movable among the unsecured, intermediate, and secured positions relative to the base element, the first mounting element may be movable among any suitable positions configured to allow a user to releasably secure the sliding assembly to the arm grip. Additionally, although second mounting element 64 is shown to be movable among the unsecured and secured positions relative to the base element, the second mounting element may be movable among any suitable positions configured to allow a user to releasably secure the arm grip to the pivot assembly. Moreover, although the first and second mounting elements are shown to be operatively connected via bias elements and thus move at least partially dependent to each other, the first and second mounting elements may be configured to move at least partially independently of each other.

Arm grip 60 also may include a handle 80, which may include any suitable structure configured to move the first mounting element among the plurality of positions described above allowing a user to releasably secure the pivot assembly and/or the sliding assembly to the arm grip. Although the arm grip is shown to include one handle, the arm grip may include two or more handles. For example, a second handle may be included to move the second mounting element among the plurality of positions described above independent of moving the first mounting element.

Additionally, arm grip 60 may include a frame 82, which may include any suitable structure configured to support and/or at least partially contain one or more other components of the arm grip. For example, the frame may include a housing 84. In some embodiments, base element 66 may be incorporated with the frame. Although the frame is shown to include base element 66, the base element may be independent from the frame.

Moreover, the arm grip may include an indicator 86, which may include any suitable structure configured to indicate to a user when the first mounting element is in one or more of its plurality of positions, when the second mounting element is in one or more of its plurality of positions, when the sliding assembly is secured to the arm grip, and/or when the pivot assembly is secured to the arm grip. For example, indicator 86 may include first stud 87 attached to the second mounting element and extend through channel 63 in the first mounting element and a channel 83 in the frame. Channels 63 and 83 allow first stud 87 to move relative to the first mounting element and the frame.

Indicator 86 also may be configured to indicate when the first mounting element is in unsecured position U1 and/or intermediate position M, such as by changing position and/or other suitable visual or non-visual indication. For example, first stud 87 may extend through channel 83 to a raised position and/or beyond the frame when the first mounting element is in unsecured position U1 in FIG. 9. In contrast, first stud 87 may not extend through channel 83 (flush to or below an external surface of the frame) in a lowered position when the first mounting element is in intermediate position M in FIG. 10. Additionally, or alternatively, the indicator may indicate when the pivot assembly is secured to the arm grip. For example, the first stud may not extend through channel 83 (flush to or below an external surface of the frame) when the arm grip receiver is not held by the arm grip receiver, and the stud may extend through channel 83 and/or beyond the frame when the arm grip receiver is held between the base element and the second mounting element of the arm grip.

Although indicator 86 is shown to include first stud 87, the indicator may include any suitable structure configured to indicate when the first mounting element is in one or more of its plurality of positions, when the second mounting element is in one or more of its plurality of positions, when the sliding assembly is secured or unsecured to the arm grip, and/or when the pivot assembly is secured or unsecured to the arm grip.

Although arm grip 60 is shown to include specific structure, the arm grip may include any suitable structure configured to releasably secure the sliding assembly to the pivot assembly. Moreover, although interconnect assembly 32 is shown to include arm grip 60, any suitable structure configured to operatively connect the pivot assembly to the sliding assembly may be used.

Sliding assembly 34 may include any suitable structure configured to allow a user to slide instrument 300 along any suitable direction(s). For example, sliding assembly 34 may include an arm assembly 88 having a first portion 90 and a second portion 92, as shown in FIG. 2. The first portion may be mounted to the pivot assembly, such as via the interconnect assembly, while the second portion may be spaced from the first portion. For example, the arm assembly may include an outer arm 94 included in first portion 90 and an inner arm 96 included in second portion 92.

The outer arm may include any suitable structure configured to be received or mounted to interconnect assembly 32, and/or to support the inner arm. Inner arm 96 may include any suitable structure configured to slide within the outer arm and/or to connect to support assembly 26. The arm assembly may extend along a longitudinal axis L. The sliding assembly also may include an inner arm retainer (not shown) configured to prevent a user from removing inner arm 96 from outer arm 94.

Although the outer and inner arms are shown to include a circular cross-section, the outer and inner arms may be include any suitable cross-section(s) configured to allow a user to slide the instrument along any suitable direction(s). Additionally, although sliding assembly 34 is shown to include outer and inner arms, any suitable structure configured to allow a user to slide instrument 300 may be used. Moreover, although sliding assembly is shown to allow a user to slide the instrument along directions perpendicular to the first and/or second pivot axes, the sliding assembly may be configured to allow a user to slide the instrument along any suitable direction(s). In some example, a sliding assembly may not be used.

The instrument support apparatus also may include support assembly 26, which may include any suitable structure configured to support instrument 300 and/or secure the instrument to the instrument support apparatus. For example, the support assembly may include a grip 98, which may be mounted to the second portion of the arm assembly via a pivot connector 99 and/or any suitable portion of the motion assembly, as shown in FIG. 2. Pivot connector 99 may include any suitable structure configured to pivot grip 98 about a grip pivot axis G relative to the arm assembly.

Grip 98 may include any suitable structure configured to support instrument 300 along any suitable axis, such as supporting the instrument with instrument axis I extending along a support axis T. Additionally, or alternatively, the grip may include any suitable structure configured to secure the instrument to the instrument support apparatus. For example, the grip may include a channel 100 and a locking mechanism 102, as shown in FIGS. 13-15.

The channel may extend along support axis T (as shown in FIG. 2). For example, channel 100 may include an opening 104, which may be sized to radially receive the shaft of instrument 300.

Locking mechanism 102 may include any suitable structure configured to secure or lock the shaft of instrument 300 relative to the grip. For example, the locking mechanism may include a locking element 106 and a handle 108. The locking element may be configured to move between a locking position K (as shown in FIG. 14) in which the locking element engages the shaft of the instrument, and an unlocking position N (as shown in FIG. 13) in which the locking element is spaced from the shaft of the instrument. The handle may include any suitable structure configured to move the locking element between the locking and unlocking positions. For example, turning handle 108 may compress locking element 106, thereby securing the instrument relative to the grip.

Figure 13:
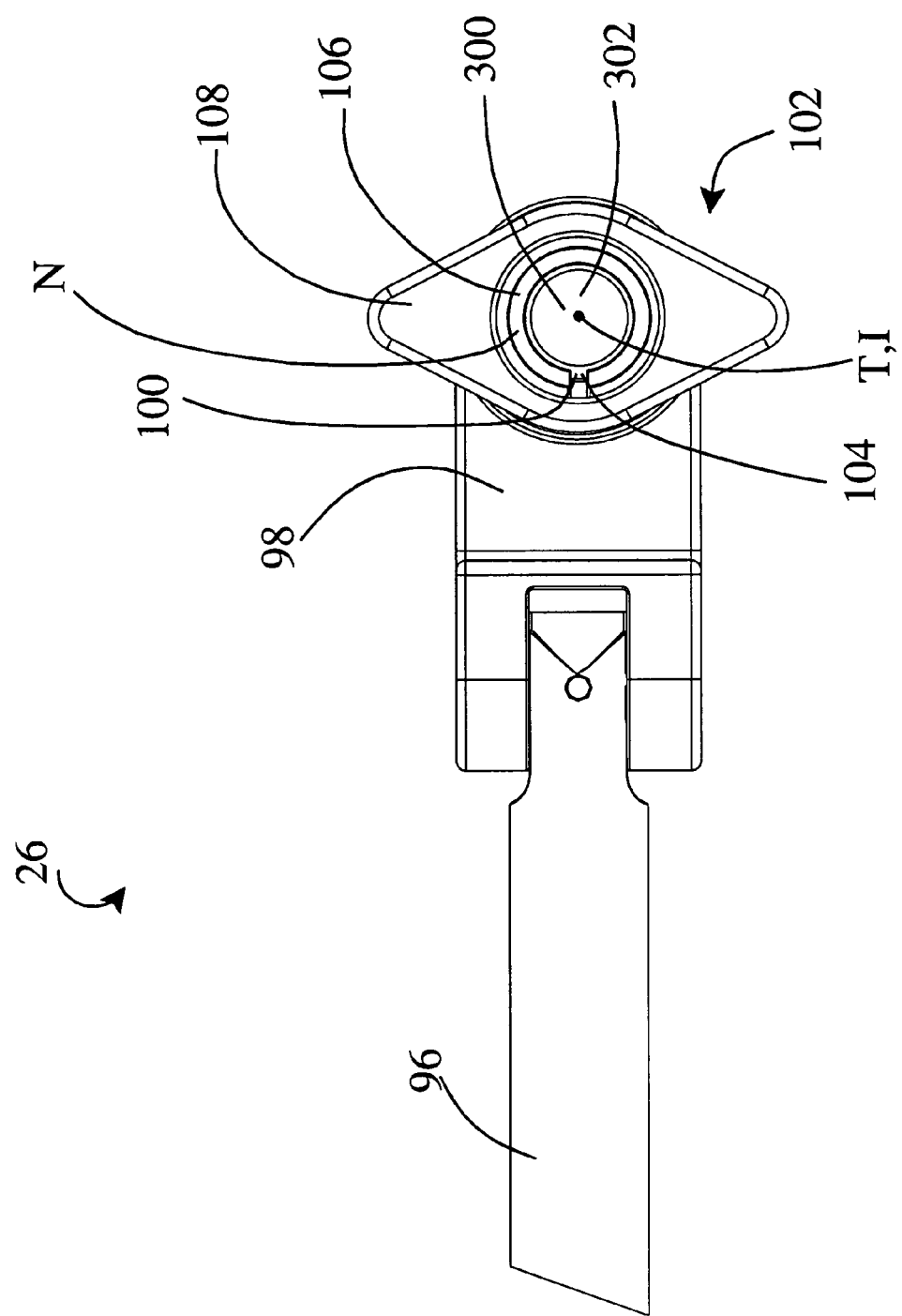
FIG. 13 is a cross-sectional view of a grip of the instrument support apparatus of FIG. 2 taken along lines 13-13, showing the grip in an unlocking position.
Figure 14:
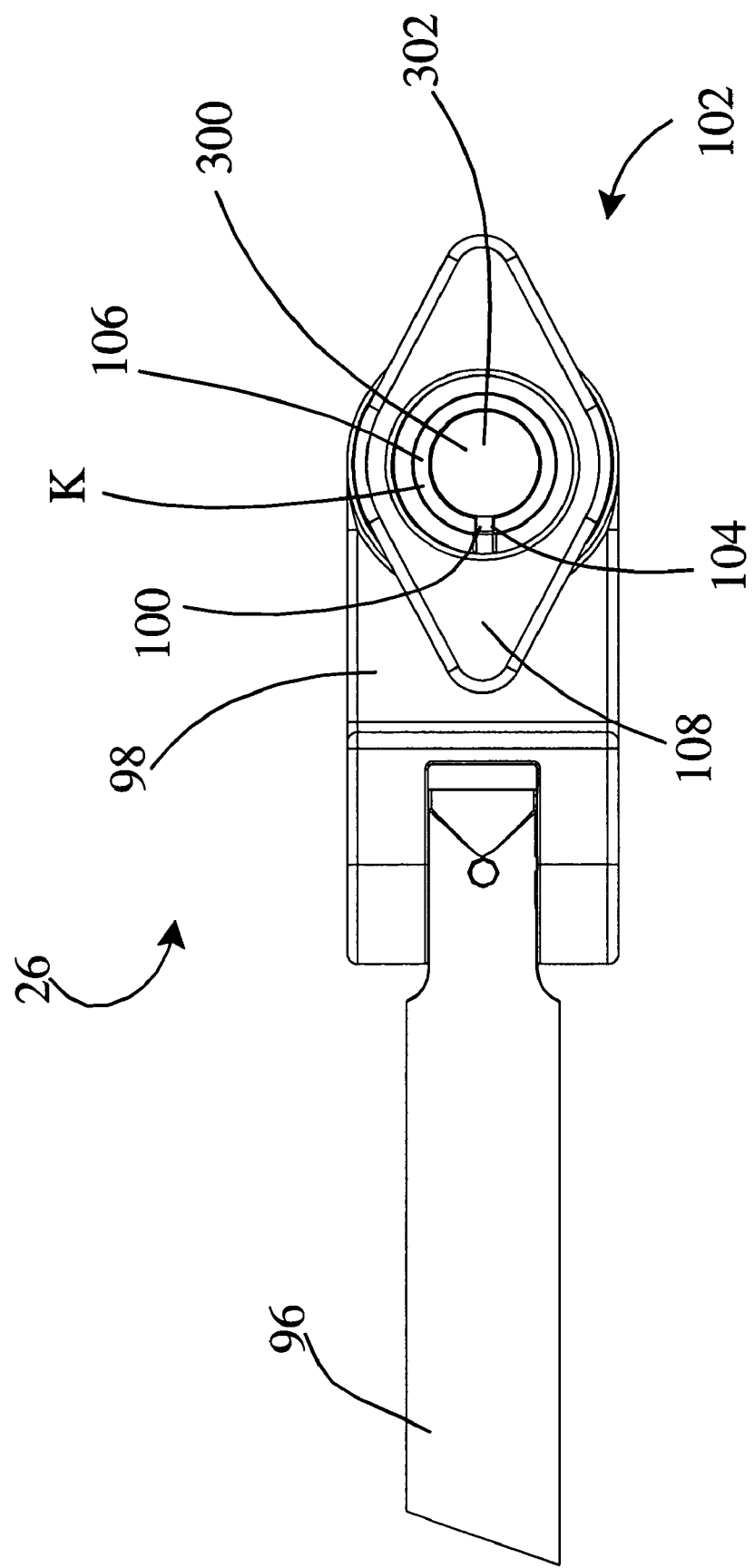
FIG. 14 is a cross-sectional view of the grip of the instrument support apparatus of FIG. 2 taken along lines 13-13, showing the grip in a locking position.
Figure 15:
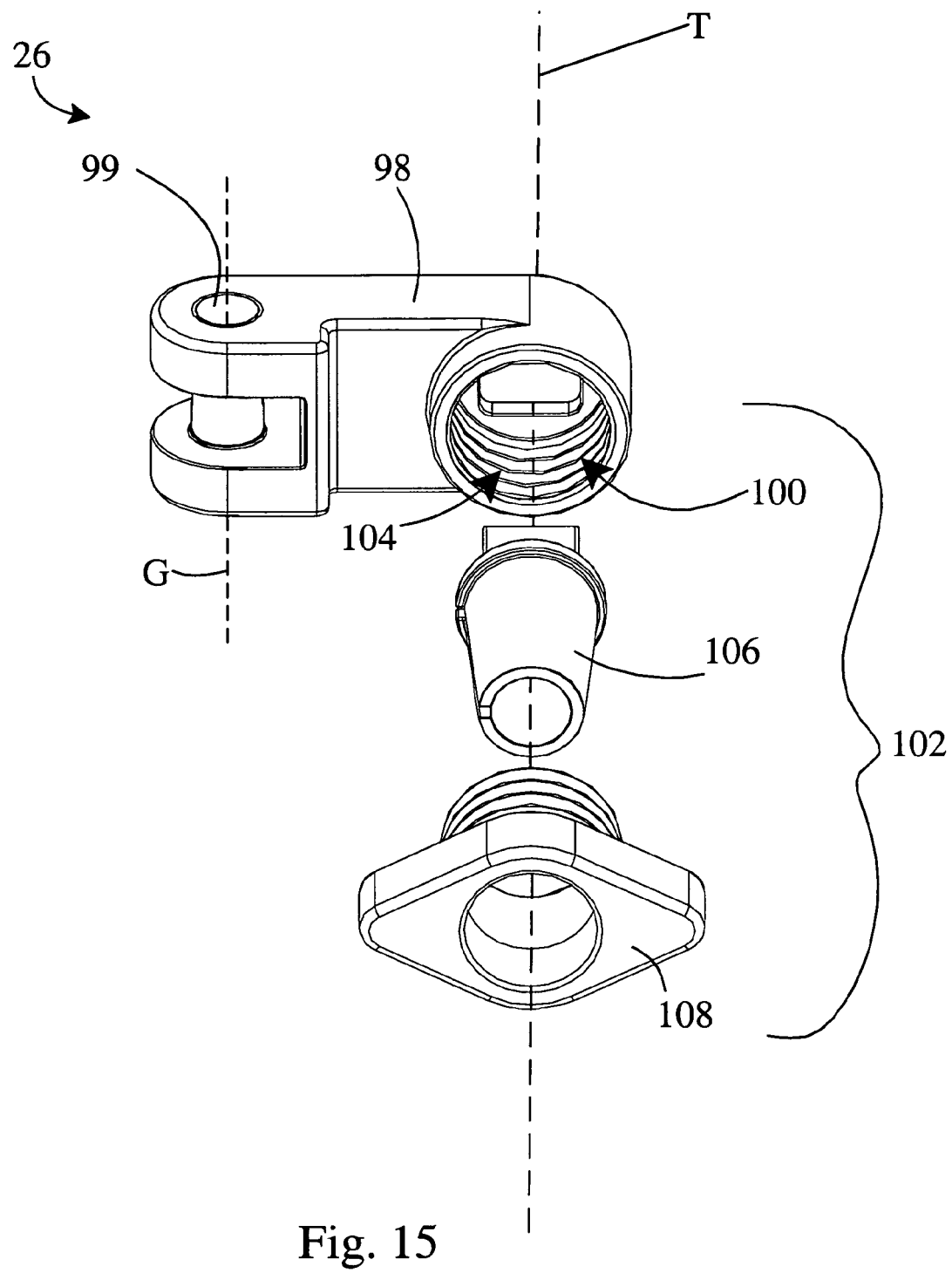
FIG. 15 is an exploded view of the grip of FIG. 13 of the instrument support apparatus of FIG. 2.
Figure 16:
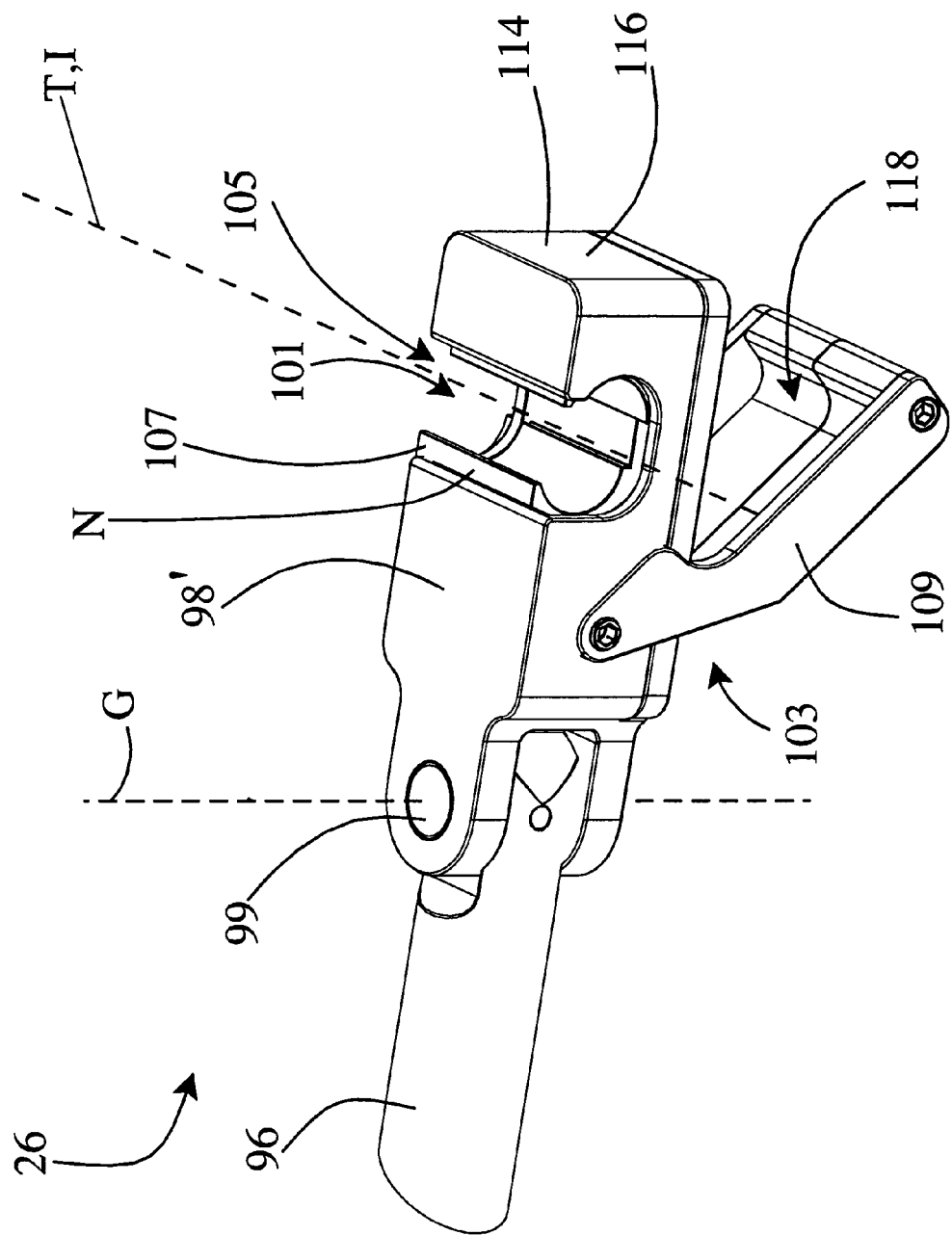
FIG. 16 is a partial view of the instrument support apparatus of FIG. 2 showing a second embodiment of a grip in an unlocking position.
Figure 17:
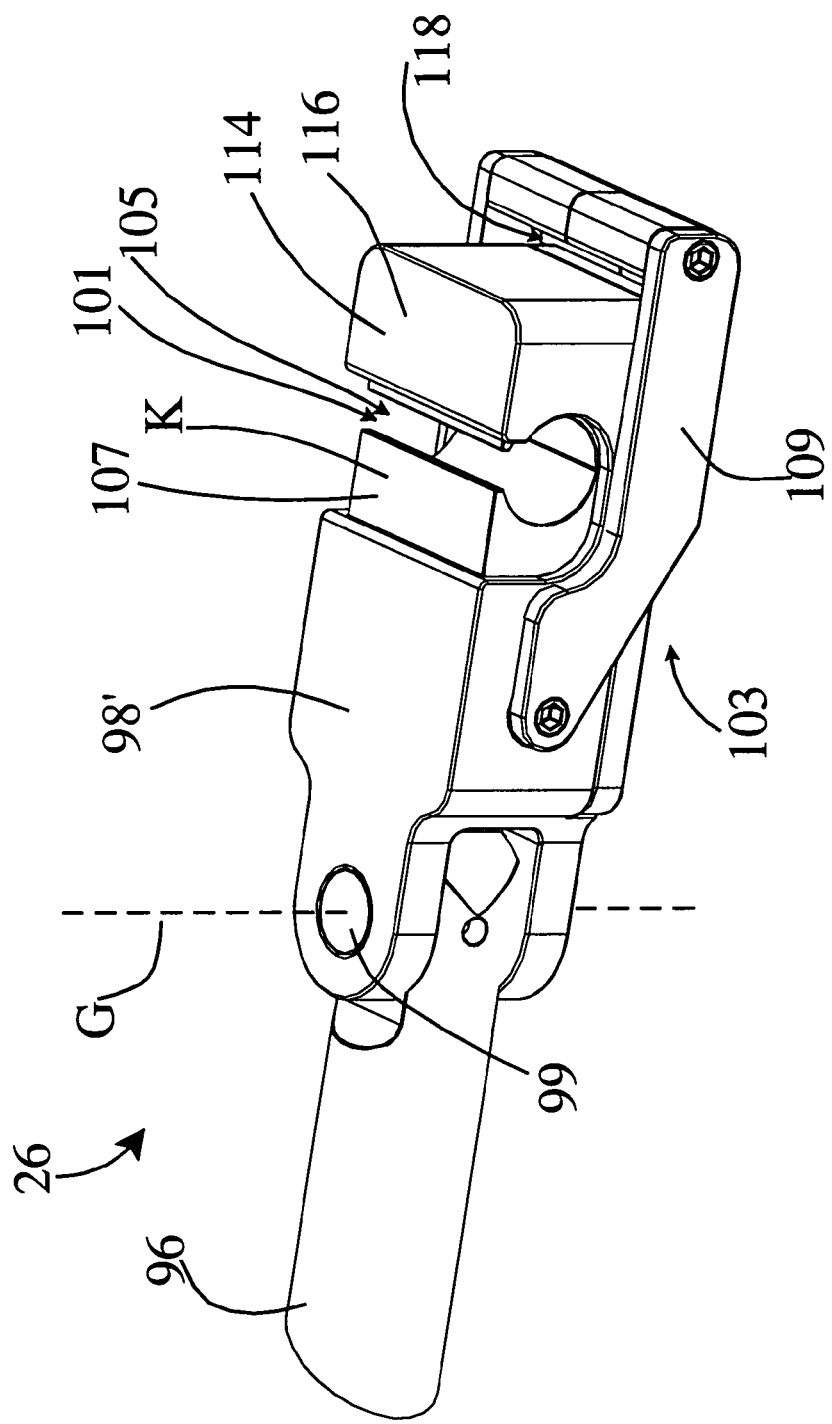
FIG. 17 is a partial view of the instrument support apparatus of FIG. 2 showing the grip of FIG. 16 in a locking position.
Figure 18:
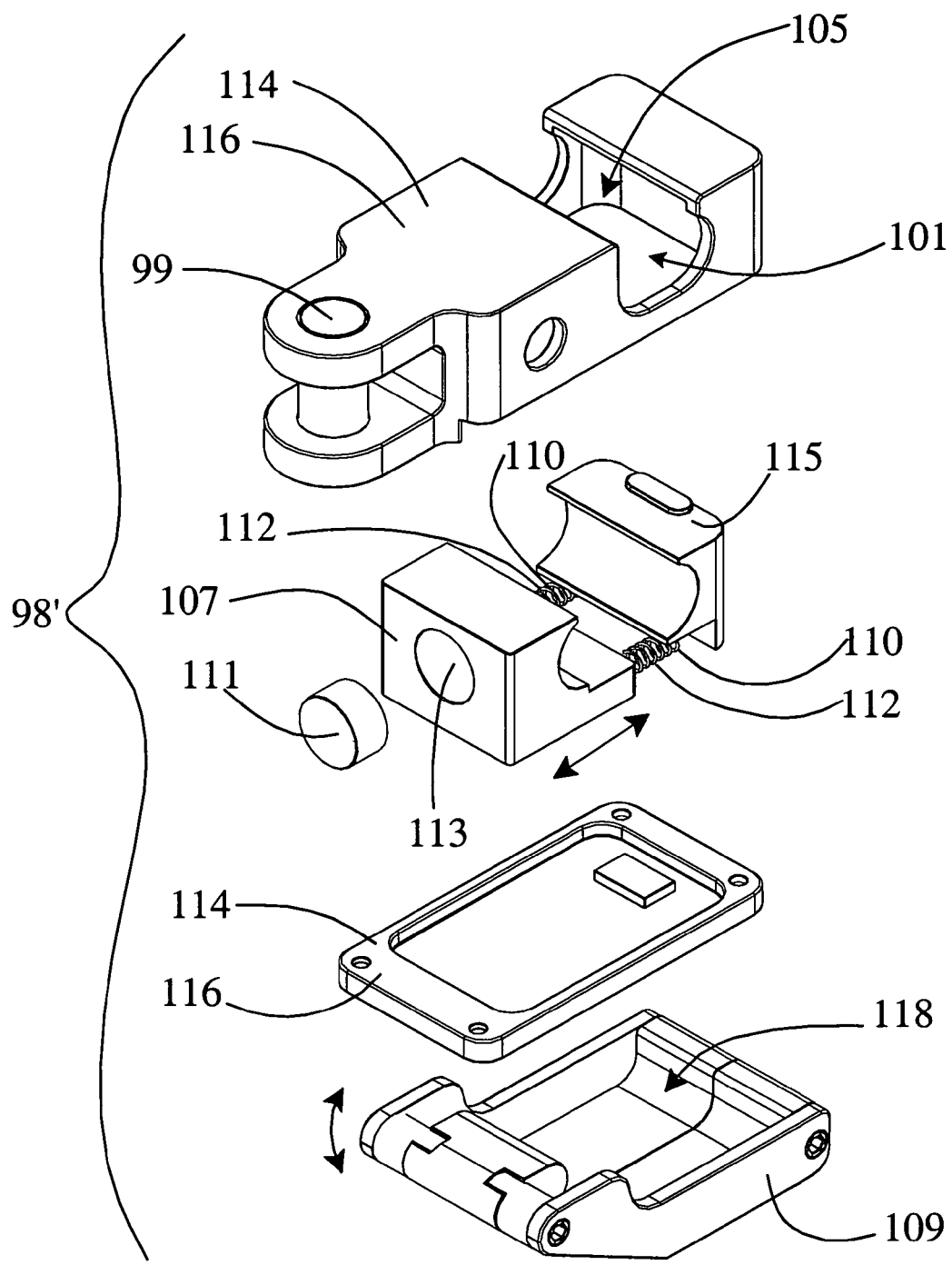
FIG. 18 is an exploded view of the grip of FIG. 16 of the instrument support apparatus of FIG. 2.

Although a specific channel and locking mechanism are shown in FIGS. 13-15, any suitable channel and/or locking mechanism may be used. For example, a grip 98' may include a channel 101 having an opening 105, which may extend laterally of the support axis, as shown in FIGS. 16-18. Opening 105 may be sized to laterally receive the shaft of instrument 300.

Additionally, grip 98 may include a locking mechanism 103 having a locking element 107 and a handle 109. The locking element may be made of any material suitable for gripping an instrument shaft, such as a resilient material. The locking element may be configured to move between a locking position K (as shown in FIG. 17) in which the locking element engages the shaft of the instrument, and an unlocking position N (as shown in FIG. 16) in which the locking element is spaced from the shaft of the instrument. With the locking element in unlocking position N, opening 105 may be large enough to freely and laterally receive the shaft of instrument 300. With the locking element in locking position K, opening 105 may be too small to allow the instrument shaft to pass through it. As a result, the instrument shaft may be securely held in position by the force of locking element 107 pressing against the instrument shaft.

The handle may include any suitable structure configured to move the locking element between the locking and unlocking positions. For example, the handle may contact an engagement member 111 mounted on a recess 113 of the locking element to move the locking element between the locking and unlocking positions.

The locking mechanism also may include one or more bias elements 110, which may include any suitable structure configured to urge the locking element towards the locking and/or unlocking positions. For example, bias elements 110 may include one or more coiled springs 112 configured to urge the locking element towards the unlocking position. Other examples may include leaf springs, music wires, and/or other suitable resilient structures. Although bias elements 110 are shown to urge locking element 107 towards the unlocking position, the bias elements may alternatively, or additionally, urge the locking element towards the locking position.

Grip 98' also may include a frame 114, which may include any suitable structure configured to support and/or at least partially contain the locking element and, in some embodiments, the bias elements. As can be seen, the frame may conform to opening 101 to allow receipt of the instrument shaft. For example, frame 114 may include housing 116. Additionally, the frame may include a resilient brace element 115, which may have a concave face opposing and matching that of locking element 107. Together, the brace element and the locking element may form a jaw that may selectively be opened and closed on the instrument shaft. Furthermore, bias elements 110 may extend between and act on the brace element and/or the locking element.

Handle 108 may be configured to conform to one or more portions of the frame, such as being flush against the frame, to provide a compact design and/or to prevent accidental movement of the handle. For example, the handle may include a recess 118, which may be sized to receive a portion of the frame when the handle is manipulated to move the locking element to the locking position.

Although the handle is shown to include recess 118, the frame alternatively, or additionally, include a recess to receive one or more portions of the handle. Additionally, although the handle is shown to be flush against the frame when the locking element is in the locking position, this position is convenient, though not necessary for the handle to function. For example, the handle may be configured to be flush against the frame when the locking element is in the unlocking position and/or any other suitable position(s).

Figure 5:
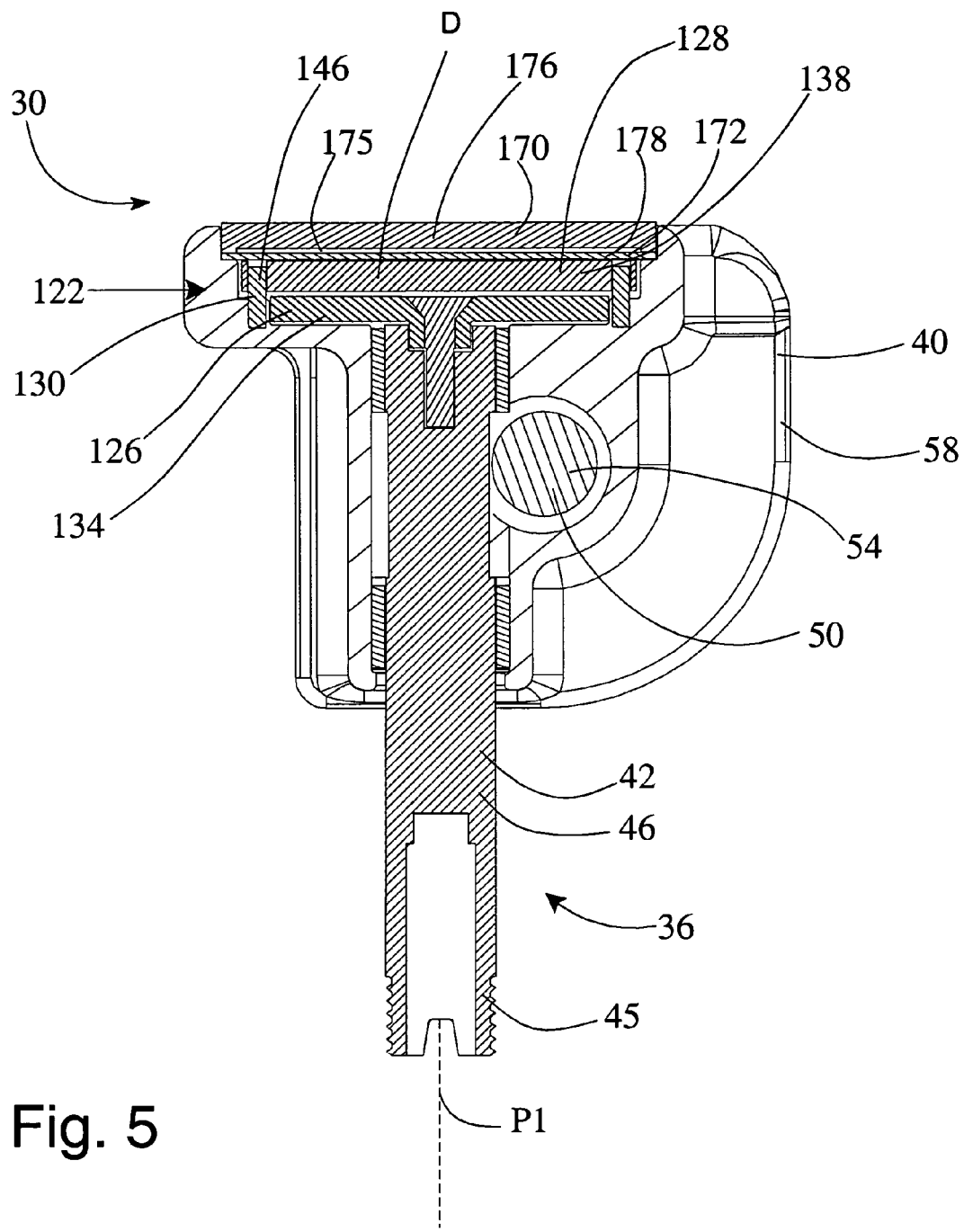
FIG. 5 is a cross-sectional view of the pivot assembly of the instrument support apparatus of FIG. 2 taken along lines 4-4 shown in FIG. 3, showing a lock assembly in the unlocking position.
Figure 6:
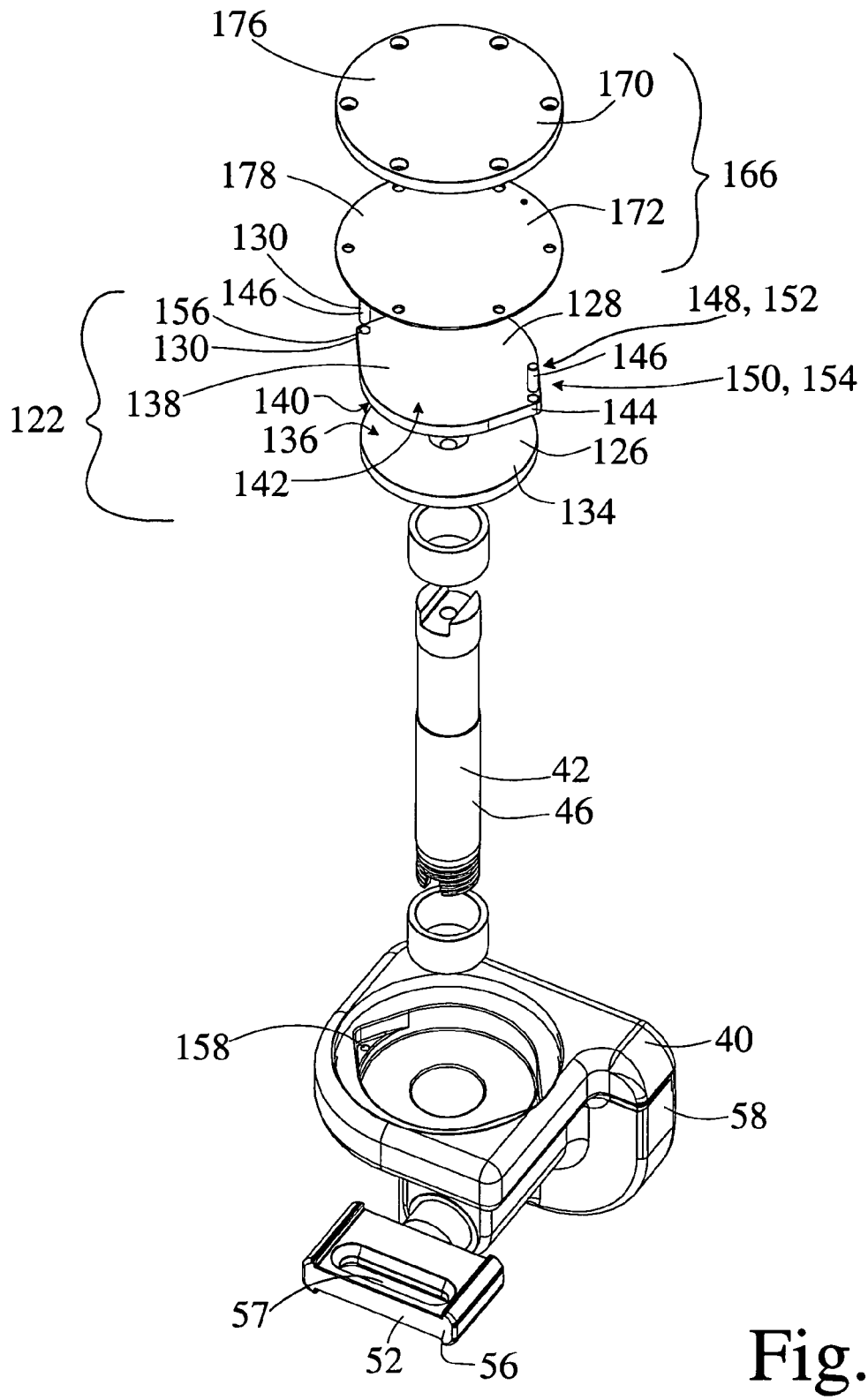
FIG. 6 is an exploded view of a first pivot structure and a first lock assembly of the pivot assembly of the instrument support apparatus of FIG. 2.

Referring now to FIGS. 1 and 4-8, instrument support apparatus 20 also may include one or more lock assemblies 120, which may include any suitable structure configured to lock movement of instrument 300. For example, lock assemblies 120 may include a first lock assembly 122 and a second lock assembly 124, as shown in FIGS. 4-7. Those lock assemblies may be mounted to or supported in any suitable location. For example, the lock assemblies may be supported via frame 40 of pivot assembly 30. The first lock assembly may include any suitable structure configured to lock first pivot structure 36 and/or prevent a user from pivoting instrument 300 about first pivot axis P1. For example, first lock assembly 122 may include a first lock element 126, a second lock element 128, and a first stop 130, as shown in FIG. 6.

First lock element 126 may include any suitable structure configured to co-pivot with first pivot element 42 about first pivot axis P1. For example, first lock element 126 may include a rotation disc 134 mounted to the first pivot element and having a first planar face 136. The second lock element may include any suitable structure configured to move between a locking position C (as shown in FIG. 4) in which the second lock element engages the first lock element, and an unlocking position D (as shown in FIG. 5) in which the second lock element is spaced from the first lock element. For example, second lock element 128 may include a compression plate 138 having a second planar face 140. When lock element 128 moves from the unlocking position to the unlocking position, face 140 may contact face 136. With plate 138 prevented from rotating, disc 134 may be frictionally prevented from rotating as well, which may thereby secure pivot element 42 in a fixed rotational position.

Second lock element 128 may be positioned at any suitable location and/or disposed to move along any suitable direction relative to the first lock element. For example, the second lock element may be positioned opposite from the first lock element (such that the second face opposes the first face and both the first and second faces are intersected by the first pivot axis) and/or be disposed to move normal to the first lock element such that the second face of the second lock element engages the first face of the first lock element. The second face may include a circular or annular region 142 or a group of spaced regions concentric with first pivot axis P1.

Although the first and second lock elements are shown to include at least substantially circular discs and plates, those lock elements may be any suitable shape. Additionally, although the second lock element is shown to be disposed to move normal to the first lock element, that lock element may be disposed to move in any suitable direction. Moreover, although the second lock element is configured to move towards the first lock element, the first lock element may alternatively, or additionally, move towards the second lock element. Furthermore, although the second lock element is shown to be positioned such that the first pivot axis intersects the second lock element at a center of the second lock element, the second lock element may be positioned in any suitable location such that the first pivot axis intersects the second lock element at other location(s) of the second lock element, such as a perimeter or an end portion of the second lock element. In some embodiments, the second lock element may be positioned such that the first pivot axis does not intersect any portion of the second lock element.

First stop 130 may include any suitable structure configured to prevent pivoting of the second lock element about first pivot axis P1. For example, first stop 130 may include at least one extension 144 extending between the second face of the second lock element and frame 40. Alternatively, or additionally, the extension may extend radially distally of the second face. Additionally, or alternatively, the extension may be incorporated with or formed integrally with the second lock element.

The first stop also may include at least one pin 146 having opposite ends or end portions 148 and 150 braced relative to the extension and the frame. Alternatively, or additionally, the opposite ends of the pin may be braced relative to the second lock element and frame 40. The pin also may have a first portion 152 and a second portion 154. The first portion may be mounted to or received by the second lock element in any suitable way. For example, the second lock element may include at least one aperture 156 that may be sized to receive the first portion of the pin. The second portion of the pin may be mounted to or received by frame 40 in any suitable way. For example, the frame may include at least one recess 158 sized to receive the second portion of the pin.

At least one pin 146 may have any suitable orientation. For example, the pin may be parallel to the first pivot axis. Other suitable orientations may be used configured to prevent the second face and/or the second lock element from pivoting about the first pivot axis. Additionally, the pin may be moveable relative to one or both of the first lock element and the frame.

Although the first stop is shown to include at least one extension and/or at least one pin, the first stop may include any suitable structure configured to prevent pivoting of the second face and/or the second lock element about the first pivot axis. For example, the shape of the frame conforming to the extension may be sufficient to prevent pivoting of the second lock element. Additionally, although the extension is shown to be incorporated with the second lock element, the extension may be independent from the second lock element. Moreover, although the at least one pin is shown to engage frame 40, the extension may alternatively, or additionally, engage the frame.

Furthermore, although the at least one pin is shown to be received in the aperture of the second lock element and the recess of the frame, the second lock element and the frame may include any suitable structure configured to secure one or more portions of the pin. Additionally, although the second lock element is shown to have two extensions and two pins, any suitable number of extensions and/or pins may be used.

Second lock assembly 124 may include any suitable structure configured to lock second pivot structure 38 and/or prevent a user from pivoting instrument 300 about second pivot axis P2. For example, second lock assembly 124 may be structured the same as or similar to first lock assembly 122, and may include a third lock element 180, a fourth lock element 182, and a second stop 184, as shown in FIG. 7.

Third lock element 180 may include any suitable structure configured to co-pivot with second pivot element 50 about second pivot axis P2. For example, third lock element 180 may include a rotation disc 186 mounted to the second pivot element and having a third planar face 188. The fourth lock element may include any suitable structure configured to move, similar to the second lock element in FIGS. 4 and 5, between locking position C in which the fourth lock element engages the third locking element, and unlocking position D in which the fourth lock element is spaced from the third lock element. For example, fourth lock element 182 may include a compression plate 190 having a fourth planar face 192.

Fourth lock element 182 may be positioned at any suitable location and/or disposed to move along any suitable direction relative to the third lock element. For example, the fourth lock element may positioned opposite from the third lock element (such that the fourth face opposes the third face and both the third and fourth faces are intersected by the second pivot axis) and/or be disposed to move normal to the third lock element such that the fourth face of the fourth lock element engages the third face of the third lock element. The fourth face may include a circular region 194 concentric with the second pivot axis.

Although the third and fourth lock elements are shown to include at least substantially circular discs and plates, those lock elements may be any suitable shape. Additionally, although the fourth lock element is shown to be disposed to move normal to the third lock element, that lock element may be disposed to move in any suitable direction. Moreover, although the fourth lock element is configured to move towards the third lock element, the third lock element may alternatively, or additionally, move towards the fourth lock element. Furthermore, although the fourth lock element is shown to be positioned such that the second pivot axis intersects the fourth lock element at a center of the fourth lock element, the fourth lock element may be positioned in any suitable location such that the second pivot axis intersects the fourth lock element at other location(s) of the fourth lock element, such as a perimeter or an end portion of the fourth lock element. In some embodiments, the fourth lock element may be positioned such that the second pivot axis does not intersect any portion of the fourth lock element.

Second stop 184 may include any suitable structure configured to prevent pivoting of the fourth lock element about second pivot axis P2. For example, second stop 184 may include at least one extension 196 extending between the fourth face of the fourth lock element and frame 40. Alternatively, or additionally, the extension may extend radially distally of the fourth face. Additionally, or alternatively, the extension may be incorporated with or formed integrally with the fourth lock element.

The second stop also may include at least one pin 198 having opposite ends 200 and 202 braced relative to the extension and the frame. Alternatively, or additionally, the opposite ends of the pin may be braced relative to the fourth lock element and frame 40. The pin also may have a first portion 204 and a second portion 206. The first portion may be mounted to or received by the fourth lock element in any suitable way. For example, the fourth lock element may include at least one aperture 208 that may be sized to receive the first portion of the pin. The second portion of the pin may be mounted to or received by frame 40 in any suitable way. For example, the frame may include at least one recess 210 sized to receive the second portion of the pin.

At least one pin 198 may have any suitable orientation. For example, the pin may be parallel to the second pivot axis. Other suitable orientations may be used configured to prevent the fourth face and/or the fourth lock element from pivoting about the second pivot axis. Additionally, the pin may be moveable relative to one or both of the third lock element and the frame.

Although the second stop is shown to include at least one extension and/or at least one pin, the second stop may include any suitable structure configured to prevent pivoting of the fourth face and/or the fourth lock element about the second pivot axis. Additionally, although the extension is shown to be incorporated with the fourth lock element, the extension may be independent from the fourth lock element. Moreover, although the at least one pin is shown to engage frame 40, the extension may alternatively, or additionally, engage the frame.

Furthermore, although the at least one pin is shown to be received in the aperture of the fourth lock element and the recess of the frame, the fourth lock element and the frame may include any suitable structure configured to secure one or more portions of the pin. Additionally, although the fourth lock element is shown to have two extensions and two pins, any suitable number of extensions and/or pins may be used.

Lock assemblies 120 also may include biasing mechanism 132, which may include any suitable structure configured to selectively bias the second lock element towards the first lock element, and/or the fourth lock element towards the third lock element, as shown in FIG. 2. For example, biasing mechanism 132 may include a supply line 162, a control device 164, a first receiving assembly 166, a second receiving assembly 212, and a channel 214, as shown in FIGS. 2 and 6-8.

Supply line 162 may include any suitable structure configured to fluidly communicate or connect a pressurized gas supply 160 to the control device and the receiving assembly. For example, the supply line may include any suitable tubing or piping. The pressurized gas supply may include any suitable supply such as a pressurized gas cylinder or tank of nitrogen or air.

Control device 164 may include any suitable structure configured to selectively regulate the pressure of the pressurized gas and/or to selectively control the flow of pressurized gas from the supply line to the receiving assembly. The control device may include remote actuators located in any suitable location, such as on the support assembly or on the laparoscope camera. Control devices are well known in the art. Illustrative examples of suitable structures are disclosed in U.S. Pat. No. 5,957,423, the complete disclosure of which has been incorporated by reference for all purposes.

First receiving assembly 166 may include any suitable structure configured to receive pressurized gas and urge the second face and/or the second lock element towards the first face and/or the first lock element. For example, receiving assembly may include a outer containment 170 and a flexible element 172.

Outer containment 170 and flexible element 172 may include any suitable structures configured to contain pressurized gas within a receiving space 175. For example, outer containment 170 may include an outer plate 176 mounted to frame 40 of pivot assembly 30. Flexible element 172 may include a rubber membrane 178 disposed between the outer plate and the frame. The outer plate and the rubber membrane may define the receiving space. Additionally, flexible element 172 may be configured to flex towards the second lock element when pressurized gas is introduced into receiving space 175, such that the second face and/or the second lock element is urged towards the first face and/or the first lock element.

Although receiving assembly 166 is shown to include outer containment 170 and flexible element 172, the receiving assembly may include any suitable structure configured to receive pressurized gas and urge the second face and/or the second lock element towards the first face and/or the first lock element. Additionally, although receiving assembly is shown to be configured to urge the second face towards the first face, the receiving assembly may additionally, or alternatively, be configured to urge the first face towards the second face.

Second receiving assembly 212 may include any suitable structure configured to receive pressurized gas and urge the fourth face and/or the fourth lock element towards the third face and/or the third lock element. For example, the second receiving assembly may include a connector 168, a outer containment 216, and a flexible element 218. Connector 168 may include any suitable structure configured to connect the receiving assembly to the biasing mechanism. For example, connector 168 may include a luer 174.

Outer containment 216 and flexible element 218 may include any suitable structures configured to contain pressurized gas within a second receiving space 220. For example, outer containment 216 may include an outer plate 222 mounted to frame 40 of pivot assembly 30. Flexible element 218 may include a rubber membrane 224 disposed between the outer plate and the frame. The outer plate and the rubber membrane may define the second receiving space. Additionally, flexible element 218 may be configured to flex towards the fourth lock element when pressurized gas is introduced into second receiving space 220, such that the fourth face and/or the fourth lock element is urged towards the third face and/or the third lock element.

Although second receiving assembly 212 is shown to include outer containment 216 and flexible element 218, the second receiving assembly may include any suitable structure configured to receive pressurized gas and urge the fourth face and/or the fourth lock element towards the third face and/or the third lock element. Additionally, although the second receiving assembly is shown to be configured to urge the fourth face towards the third face, the second receiving assembly may additionally, or alternatively, be configured to urge the third face towards the fourth face.

Figure 8:
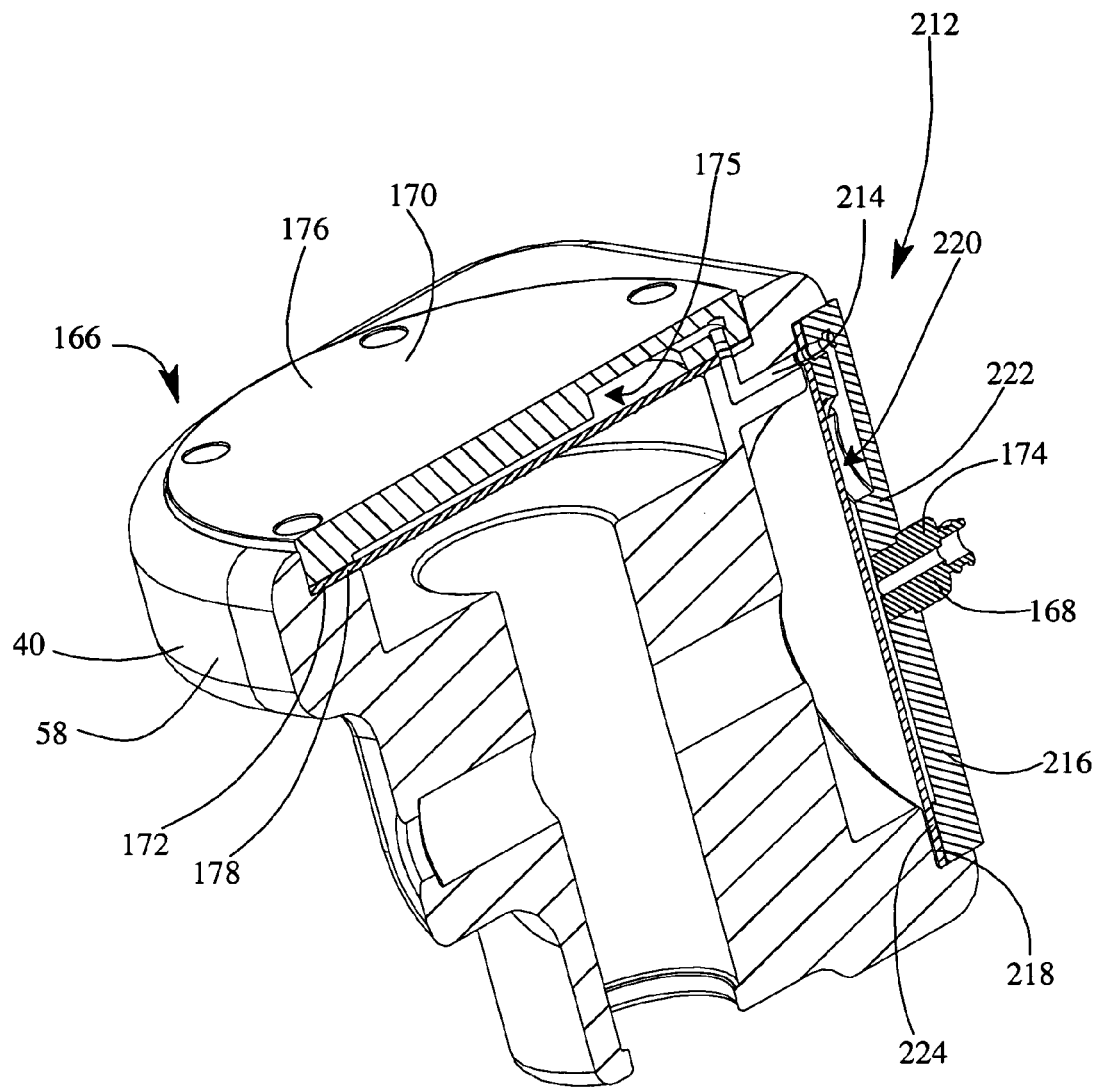
FIG. 8 is a cross-sectional isometric view of a portion of the pivot assembly of the instrument support apparatus of FIG. 2 taken along lines 8-8 shown in FIG. 3, showing first and second receiving assemblies with a gas connecting channel fluidly connecting the two assemblies, and shown without first and second pivot elements and first and second lock assemblies.

Channel 214 may include any suitable structure configured to fluidly connect the first receiving assembly and the second receiving assembly. For example, the channel may connect receiving space 175 of the first receiving assembly with receiving space 220 of the second receiving assembly, as shown in FIG. 8. Although biasing mechanism 132 is shown to interact with the first and second locking assemblies, separate biasing mechanisms may be provided for each lock assembly. Additionally, although the first and second receiving assemblies and channel 214 are shown to be at least partially contained within frame 40 of pivot assembly 30, one or both assemblies and/or that channel may be at least partially external the frame.

Lock assemblies 120 of instrument support apparatus 20 also may include a third lock assembly 226, as shown in FIG. 2. That lock assembly may be mounted to or supported in any suitable location. For example, third lock assembly 226 may be mounted to arm assembly 88 of sliding assembly 34. The third lock assembly may include any suitable structure configured to lock sliding assembly and/or prevent a user from sliding instrument 300 along longitudinal axis L. Third lock assembly 226 may include one or more components that are the same as or similar to the components of the first and/or second lock assemblies. Additionally, or alternatively, the third lock assembly may include one or more components of the locking assemblies disclosed in U.S. Pat. No. 5,957,423, the complete disclosure of which has been incorporated by reference for all purposes. Moreover, biasing mechanism 132 may be configured to interact with the third lock assembly, or a separate biasing mechanism may be provided for the third lock assembly.

Although instrument support apparatus 20 is shown to include the first, second, and third lock assemblies, any suitable number of lock assemblies may be used. Additionally, although the first and second lock assemblies are shown to include similar components, those assemblies may have different components. Moreover, although the first and second lock assemblies are shown to be at least partially contained within the frame of pivot assembly 30, one or both lock assemblies may be at least partially external the frame.

Although the instrument support apparatus and features of the instrument support apparatus have been shown and described with reference to the foregoing operational principles and preferred embodiments, those skilled in the art will find apparent that various combinations of features may be used that may be less than all of the features shown, and changes in form and detail may be made without departing from the spirit and scope of the claims. The present disclosure is intended to embrace all such alternatives, modifications, and variances that fall within the scope of the appended claims.

What is claimed is:

1. An instrument support apparatus for supporting an instrument having a shaft extending along a shaft axis relative to a patient positioned adjacent to an external frame, comprising:
   a base fixedly mountable onto the external frame;
   a pivot assembly mounted relative to the base and including a frame, a first pivot element pivotably mounted to the frame and fixedly mounted to the base, and a second pivot element pivotably mounted to the frame, the frame being configured to pivot relative to the first pivot element and the external frame about a first pivot axis, the second pivot element being configured to pivot relative to the frame about a second pivot axis;
   an arm assembly extending along a longitudinal axis and having an outer arm mounted to the second pivot element for pivoting relative to the frame, and an inner arm configured to slide within the outer arm and pivot about the longitudinal axis relative to the outer arm;
   a support assembly mounted to the inner arm and configured to support the instrument on the arm assembly; and
   a first lock assembly mounted to the frame and configured to be remotely actuated to lock the frame relative to the first pivot element, wherein the first lock assembly includes first and second opposing planar faces intersected by the first pivot axis, a first stop, and a biasing mechanism, wherein the first face is mounted to the first pivot element, wherein the second face is disposed to move normal to the first face, wherein the first stop is configured to prevent pivoting of the second face relative to the frame about the first pivot axis, and wherein the biasing mechanism is configured to selectively bias the second face toward the first face.

2. The instrument support apparatus of claim 1, wherein the second face includes a circular region concentric with the first pivot axis.

3. The instrument support apparatus of claim 1, wherein the first stop includes an extension extending between the second face and the frame.

4. The instrument support apparatus of claim 3, wherein the lock assembly includes a second lock element having the second face, and the extension extends radially distally of the second face.

5. The instrument support apparatus of claim 4, wherein the extension is formed integrally with the second lock element.

6. The instrument support apparatus of claim 3, wherein the first stop includes a pin having opposite ends braced relative to the extension and the frame, respectively.

7. The instrument support apparatus of claim 3, wherein the lock assembly includes a second lock element having the second face, wherein the first stop includes a pin having opposite ends braced relative to the second lock element and the frame.

8. The instrument support apparatus of claim 7, wherein the pin includes first and second portions, wherein the second lock element includes at least one aperture sized to receive the first portion of the pin, and wherein the frame is configured to secure the second portion of the pin.

9. The instrument support apparatus of claim 8, wherein the frame includes at least one recess sized to receive the second portion of the pin.

10. The instrument support apparatus of claim 7, wherein the pin is parallel to first pivot axis, and wherein the pin is movable relative to one or both of the second lock element and the frame.

11. The instrument support apparatus of claim 1, wherein the biasing mechanism includes a control device connected to a pressurized gas supply, wherein the control device is configured to selectively provide pressurized gas to the first lock assembly to urge the second face towards the first face.

12. The instrument support apparatus of claim 1, wherein the second pivot axis is at least substantially perpendicular to the first pivot axis.

13. The instrument support apparatus of claim 1, further comprising a second lock assembly mounted to the frame and configured to be remotely actuated to lock the second pivot element, wherein the second lock assembly includes third and fourth opposing planar faces and a second stop, the third face is mounted to the second pivot element for co-pivoting with the second pivot element, the fourth face is disposed to move normal to the third face, and the second stop is configured to prevent pivoting of the fourth face about the second pivot axis.

14. The instrument support apparatus of claim 13, wherein the biasing mechanism is configured to selectively bias the fourth face towards the third face.

15. The instrument support apparatus of claim 13, wherein the biasing mechanism includes a control device connected to a pressurized gas supply, wherein the control device is configured to selectively provide pressurized gas to the first lock assembly to urge the second face towards the first face.

16. The instrument support apparatus of claim 15, wherein the control device is configured to selectively provide the pressurized gas to the second lock assembly to urge the fourth face towards the third face.

17. An instrument support apparatus for supporting an instrument having a shaft extending along a shaft axis relative to a patient positioned adjacent to an external frame, comprising:
   a base fixedly mountable onto the external frame; a pivot assembly mounted relative to the base and including a frame, a first pivot element pivotably mounted to the frame and fixedly mounted to the base, and a second pivot element pivotably mounted to the frame, the frame being configured to pivot relative to the first pivot element and the external frame about a first pivot axis, the second pivot element being configured to pivot relative to the frame about a second pivot axis;
   an arm assembly extending along a longitudinal axis and having a first portion mounted to the second pivot element for pivoting relative to the frame, and a second portion spaced from the first portion and configured to pivot about the longitudinal axis relative to the first portion, wherein the first pivot and second pivot axes are orthogonal to each other when viewed from a plane parallel to those axes, and the second pivot and longitudinal axes are orthogonal to each other when viewed from a plane parallel to those axes;
   a support assembly mounted to the second portion and configured to support the instrument on the arm assembly; and a first lock assembly mounted to the frame and configured to be remotely actuated to lock the frame relative to the first pivot element, wherein the first lock assembly includes first and second opposing planar faces intersected by the first pivot axis, a first stop, and a biasing mechanism, the first face being mounted to the first pivot element, the second face being disposed to move normal to the first face, the first stop being configured to prevent pivoting of the second face relative to the frame about the first pivot axis, the biasing mechanism including a control device connected to a pressurized gas supply, the control device being configured to selectively bias the second face toward the first face.

18. The instrument support apparatus of claim 17, wherein the first portion of the arm assembly includes an outer arm, and the second portion of the arm assembly includes an inner arm, the inner arm being configured to slide within the outer arm and to pivot about the longitudinal axis relative to the outer arm.

19. The instrument support apparatus of claim 18, further comprising a second lock assembly mounted to the frame and configured to be remotely actuated to lock the second pivot element.

20. The instrument support apparatus of claim 19, further comprising a third lock assembly mounted to the arm assembly and configured to lock and prevent the inner arm from sliding within the outer arm and from pivoting about the longitudinal axis.

21. The instrument support apparatus of claim 17, wherein the pivot assembly further includes a first flexible membrane disposed adjacent to the second face and configured to flex toward the second face, and wherein the control device is configured to selectively flex the first flexible membrane to move the second face toward the first face.

22. The instrument support apparatus of claim 21, wherein the frame includes an outer containment adjacent to the flexible membrane, the outer containment and the flexible element defining a receiving space configured to contain pressurized gas from the control device.

23. The instrument support apparatus of claim 17, wherein the frame includes a first frame aperture and a second frame aperture, the first frame aperture being configured to pivotably receive the first pivot element, the second frame aperture being configured to pivotably receive the second pivot element, the first frame aperture at least partially intersecting the second frame aperture.

24. An instrument support apparatus for supporting an instrument having a shaft extending along a shaft axis relative to a patient positioned adjacent to an external frame, comprising:
a base fixedly mountable onto the external frame;
a pivot assembly mounted relative to the base and including a frame, a first pivot element pivotably mounted to the frame and fixedly mounted to the base, and a second pivot element pivotably mounted to the frame, the frame being configured to pivot relative to the first pivot element and the external frame about a first pivot axis, the second pivot element being configured to pivot relative to the frame about a second pivot axis;
an arm assembly extending along a longitudinal axis and having a first portion mounted to the second pivot element for pivoting relative to the frame, and a second portion spaced from the first portion and configured to pivot about the longitudinal axis relative to the first portion;
a support assembly mounted to the second portion and configured to support the instrument on the arm assembly; and
a first lock assembly mounted to the frame and configured to be remotely actuated to lock the frame relative to the first pivot element, wherein the first lock assembly includes a first flexible membrane, first and second opposing planar faces intersected by the first pivot axis, a first stop, and a biasing mechanism, the first face being mounted to the first pivot element, the second face being disposed to move normal to the first face, the first flexible membrane being disposed adjacent to the second face and configured to flex toward the second face, the first stop being configured to prevent pivoting of the second face relative to the frame, the biasing mechanism including a control device connected to a pressurized gas supply, the control device being configured to selectively flex the first flexible membrane to move the second face toward the first face.

25. The instrument support apparatus of claim 24, wherein the frame includes a first outer containment adjacent to the first flexible membrane, the first outer containment and the first flexible element defining a first receiving space configured to contain pressurized gas from the control device.

26. The instrument support apparatus of claim 25, further comprising a second lock assembly mounted to the frame and configured to be remotely actuated to lock the second pivot element, wherein the second lock assembly includes a second stop and third and fourth opposing planar faces intersected by the second pivot axis, wherein the third face is mounted to the second pivot element for co-pivoting with the second pivot element, wherein the fourth face is disposed to move normal to the third face, wherein the second stop is configured to prevent pivoting of the fourth face about the second pivot axis, and wherein the biasing mechanism is further configured to selectively bias the fourth face toward the third face.

27. The instrument support apparatus of claim 26, wherein the pivot assembly further includes a second flexible membrane disposed adjacent to the fourth face and configured to flex toward the fourth face, and wherein the control device is further configured to selectively flex the second flexible membrane to move the fourth face toward the third face.

28. The instrument support apparatus of claim 27, wherein the frame further includes a second outer containment adjacent to the second flexible membrane, the second outer containment and the second flexible element defining a second receiving space configured to contain pressurized gas from the control device.

29. The instrument support apparatus of claim 28, wherein the frame further includes a channel fluidly connecting the first and second receiving spaces.

30. The instrument support apparatus of claim 28, wherein the frame further includes a single connector that fluidly connects the first and second receiving spaces to the control device.

31. The instrument support apparatus of claim 24, wherein the first portion of the arm assembly includes an outer arm, and the second portion of the arm assembly includes an inner arm, the inner arm being configured to slide within the outer arm and to pivot about the longitudinal axis relative to the outer arm.

32. The instrument support apparatus of claim 31, further comprising a second lock assembly mounted to the frame and configured to be remotely actuated to lock the second pivot element.

33. The instrument support apparatus of claim 32, further comprising a third lock assembly mounted to the arm assembly and configured to lock and prevent the inner arm from sliding within the outer arm and from pivoting about the longitudinal axis.

34. The instrument support apparatus of claim 24, wherein the frame includes a first frame aperture and a second frame aperture, the first frame aperture being configured to pivotably receive the first pivot element, the second frame aperture being configured to pivotably receive the second pivot element, the first frame aperture at least partially intersecting the second frame aperture.

* * * * *